United States Patent [19]
Linhart et al.

[11] Patent Number: 5,856,550
[45] Date of Patent: Jan. 5, 1999

[54] ENHANCEMENT OF THE STORAGE STABILITY OF ORGANIC PHOSPHITES AND PHOSPHONITES

[75] Inventors: Helmut Linhart, Reinach, Switzerland; Udo Quotschalla, Mobile, Ala.; Jean-Roch Pauquet, Kaiseraugst, Switzerland; Ronald Salathé, Magden, Switzerland; Jürg Zingg, Reinach, Switzerland

[73] Assignee: Ciba Specialty Chemicals Corporation, Tarrytown, N.Y.

[21] Appl. No.: 867,112

[22] Filed: Jun. 2, 1997

Related U.S. Application Data

[63] Continuation-in-part of Ser. No. 725,103, Oct. 2, 1996, abandoned, which is a continuation-in-part of Ser. No. 413,558, Mar. 30, 1995, abandoned.

[30] Foreign Application Priority Data

Apr. 5, 1994 [CH] Switzerland ................ 985/94

[51] Int. Cl.⁶ .............. C07F 9/141; C07F 9/48
[52] U.S. Cl. ................................. 558/71
[58] Field of Search ............................. 558/71

[56] References Cited

U.S. PATENT DOCUMENTS

| | | | |
|---|---|---|---|
| 3,240,751 | 3/1966 | Cannon et al. | 558/71 |
| 3,553,298 | 1/1971 | Hodon et al. | 260/967 |
| 3,787,537 | 1/1974 | DeMarca | 260/954 |
| 4,086,304 | 4/1978 | Hutton et al. | 558/71 |
| 4,965,301 | 10/1990 | Leininger | 524/101 |
| 5,208,362 | 5/1993 | Glass et al. | 558/146 |
| 5,342,978 | 8/1994 | Enlow et al. | 554/78 |
| 5,371,263 | 12/1994 | Quotschalla et al. | 558/71 |

FOREIGN PATENT DOCUMENTS

| | | |
|---|---|---|
| 2064606 | 10/1993 | Canada . |
| 2097674 | 12/1993 | Canada . |
| 0143464 | 6/1985 | European Pat. Off. . |
| 0168721 | 1/1986 | European Pat. Off. . |
| 0167969 | 11/1986 | European Pat. Off. . |
| 0576833 | 1/1994 | European Pat. Off. . |
| 0592363 | 2/1994 | European Pat. Off. . |
| 0592364 | 4/1994 | European Pat. Off. . |
| 293477 | 10/1983 | German Dem. Rep. . |
| 56-113790 | 9/1981 | Japan . |
| 4255743 | 4/1992 | Japan . |
| 2278362 | 11/1994 | United Kingdom . |

OTHER PUBLICATIONS

Derwent Abstract AB JP 56113790A.
Derwent Abst. 92–353585/43 of JP 4–255743 (1992).
Derwent Abst. 91–076167; Japan Kokai No. 3–021651 published on Jan. 30, 1991.
Derwent Abst. 91–003847; Japan Kokai No. 2–28106 published on Nov. 16, 1990.
Derwent Abst. 94–360221; GB2278362, published on Nov. 30, 1994.
Patent Abst. of Japan, vol. 5, No. 194 (C–082) of JP 56113790, Dec. 10, 1981.
Chem. Abst. 122:11484 of EP 592,363 (1995).
Chem. Abst. 118:2567252 of JP04334810 (1993).
Derwent Abst. 94–009180/02 of EP 0576833 (1994).
Derwent Abst. 92–042074/06 of DD 293,477 (1992).
Chem. Abst. 118:192984y of JP 4255743 (1993).

*Primary Examiner*—Michael G. Ambrose
*Attorney, Agent, or Firm*—Luther A. R. Hall

[57] ABSTRACT

Described are compositions comprising (a) 25 to 99% of organic phosphite or phosphonite, based on the total weight of the composition, (b) an effective stabilizing amount of organic amine, and (c) an effective stabilizing amount of acid-binding metal salt, wherein said composition comprises no organic polymers or alkali metal phosphates as further components, as well as a process for stabilising organic phosphites or phosphonites against hydrolysis by addition of organic amine and acid-binding metal salt. The compositions are distinguished by their excellent stability to hydrolysis and have good storage stability even at high atmospheric humidity. The novel compositions and process products can be used with advantage as stabilisers for organic material against the harmful action of heat, oxygen and/or light.

14 Claims, No Drawings

ENHANCEMENT OF THE STORAGE STABILITY OF ORGANIC PHOSPHITES AND PHOSPHONITES

This application is a continuation-in-part of application Ser. No. 08/725103, filed Oct. 2, 1996, now abandoned, which is a continuation-in-part of application Ser. No. 08/413,558, filed Mar. 30, 1995 now abandoned.

The invention relates to a process for stabilising organic phosphites and phosphonites against hydrolysis by addition of amines and acid-binding metal salts, to compositions comprising these three components, and to the use of amines together with acid-binding metal salts as hydrolysis stabilisers for phosphites and phosphonites.

Organic phosphites and phosphonites are widely used as heat stabilisers for synthetic polymers.

The preparation, storage and use of phosphites and phosphonites is, however, impeded by the fact that these compounds hydrolise very easily. A particular problem is the storage of the material at high atmospheric humidity.

Different methods have been proposed to provide products having enhanced stability to hydrolysis. Besides processes for the preparation of purer products and methods of purifiying the compounds, such methods are in particular the addition of special stabilisers which on the one hand reduce the tendency of the products to hydrolyse and which, on the other hand, do not have any negative effects in the subsequent use of the phosphites or phosphonites in organic polymers.

The last mentioned methods embrace the addition of amines as hydrolysis stabilisers as is disclosed, inter alia, in U.S. Pat. No. 3,553,298. Further publications relating to the stabilisation of phosphites with amines are U.S. Pat. No. 3,787,537, U.S. Pat. No. 5,342,978, EP-A-168 721 and EP-A-167 969. It is recommended in particular to use tertiary alkanolamines and alkylamines, pyridines and anilines; typical examples are triethylamine, diethanolamine, triethanolamine, di- and triisopropanolamine (TIPA), tetraisopropanolethylenediamine, aniline, phenylenediamine and hexamethylenetetramine. The amines are generally used in amounts of up to c. 5% by weight (based on the phosphite to be stabilised). The incorporation of the amine is carried out by dry milling or by dissolution in, or mixing with, the phosphite melt and subsequent crystallisation.

The isolated use of acid-binding metal salts as hydrolysis stabiliser for phosphites has also been disclosed (CA-A-2 097 674, U.S. Pat. No. 5,208,362).

In spite of the known methods discussed above for enhancing the stability to hydrolysis of organic phosphites and phosphonites there is still a need for further improvement.

It has now been found that the combined addition of amines and acid-binding metal salts surprisingly enhances the stability to hydrolysis of organic phosphites and phosphonites. Accordingly, the invention relates to a composition comprising (a) 25 to 99.9% by weight, based on the total weight of the composition, of organic phosphite or phosphonite, (b) an effective stabilizing amount of organic amine, and (c) an effective stabilizing amount of acid-binding metal salt, wherein said composition comprises no organic polymers or alkali metal phosphates as further components.

A composition according to the invention contains, for example, 0.001 to 50 parts by weight of organic amine, and 0.01 to 25 parts by weight of acid-binding metal salt.

The phosphites and phosphonites stabilised according to this invention are distinguished by their excellent stability to hydrolysis and have good storage stability even at high humidity.

A particularly interesting composition comprises (a) 25 to 99.9% by weight of organic phosphite or phosphonite, (b) 0.01 to 50% by weight of organic amine, and (c) 0.5 to 25% by weight of acid-binding metal salt, each based on the total weight of the composition.

The content of phosphite and/or phosphonite in the stabilised composition is often 40 to 99% by weight, preferably 70 to 99% by weight and, most preferably 0 to 99% by weight.

The organic phosphite or phosphonite stabilised according to this invention usually contains 0.01 to 25% by weight of compontent (b). The stabilised phosphite or phosphonite preferably comprises an amine (component [b]) in an amount of 0.01 to 20% by weight, preferably of 0.05 to 15% by weight and, most preferably, of 0.1 to 10% by weight, in each case based on the total weight of the composition.

Component (c) is usually used in the novel composition in an amount of 0.05 to 15% by weight, preferably of 0.1 to 10% by weight and, most preferably, of 0.1 to 5% by weight.

Accordingly, a preferred composition comprises 40 to 99% by weight of component (a), 0.01 to 25% by weight of component (b) and 0.05 to 15% by weight of component (c), in each case based on the total weight of the composition.

It is preferred that, in addition to components (a), (b) and (c) the novel compositions do not comprise organic polymers as further components, for example those having a molecular weight higher than 5000. Preferred compositions comprise, in addition to components (a), (b) and (c), no further main components, or possibly 1 or 2 further main components which can also be used as stabilisers, e.g. as antioxidants, heat stabilisers or light stabilisers for synthetic polymers. These compositions will be referred to as consisting essentially of these components.

Further main components will be understood in this context as meaning those additives which are mixed with the novel composition and which constitute no impurities such as those resulting from the synthesis or from the storage or partial degradation of one of components (a) to (c).

Among these composition, those compositions which comprise no further main components are particularly preferred.

In compositions of the invention comprising 1 or 2 further main components, these are preferably phenolic or other antioxidants, selected for example among the following compounds:

1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy5'-methylbenzyl)-6-tert-butyl-4-methylphenyl]terephthalate, 1,1-bis-(3,5-dimethyl-2hydroxyphenyl)butane, 2,2-bis-(3,5-di-tert-butyl-4-hydroxyphenyl)propane, 2,2-bis-(5-tert-butyl-4-hydroxy2-methylphenyl)-4-hydroxy2-methenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4hydroxy-3,5-di-tert-butylbenzylmercaptoacetate, tris(3,5-di-tert-butyl-4-hydroxybenzyl)-amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p- phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, Bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

Preferred are phenolic antioxidants, for example those listed above under 1.1–1.17, especially the compounds oentaerythrityl-tetrakis(3-[3',5'-di-tert.butyl-4'-hydroxyphenyl]-propionate) and octadecyl-3-[3',5'-di-tert.butyl-4'-hydroxyphenyl] propionate.

Each of components (a) to (c) can be a single compound or a mixture of compounds. In the case of a compound mixture, the amounts stated indicate the total amount of the compounds used for each component.

Phosphites or organic phosphites are taken to mean compounds of formula $P(OR)_3$, wherein the substitutents R are hydrocarbon radicals which may contain hetero atoms, and furthermore at most 2 of the 3 substitutents R may be hydrogen atoms. Hetero atoms are all atoms except carbon atoms and hydrogen atoms, preferably N, O, F, Si, P, S, Cl, Br, Sn and I.

Phosphonites are esters of phosphonous acid of formula $P(OR)_2R$, wherein R has the meanings indicated above, or may be halogen.

The phosphite or phosphonite of component (a) is preferably a solid at 20° C. and is usually a crystalline solid.

The acid-binding metal salts used as component (c) in the novel compositions are usually carbonates, bicarbonates, carboxylates, oxides, hydroxides, phosphites, borates or corresponding mixed crystals, in particular of the metals lithium, sodium, potassium, copper, zinc, magnesium, calcium, strontium, barium, aluminium and/or zirconium, as well as hydrotalcites or zeolites. It is also possible to use several different acid-binding metal salts.

Of special technical interest are those acid-binding metal salts of component (c), which are no metal carboxylates or metal soaps.

Suitable acid-binding metal salts for use according to this invention are naturally occuring minerals as well as synthetically produced compounds. The metals can be partially interchanged. Said metals are crystalline, partially crystalline or amorphous, or can be obtained in the form of a dried gel.

The compounds of component (c) are expediently used in powdered form. The crystallites in the powder preferably have a high specific surface. Said high specific surface can be achieved by corresponding fine graining and/or a porous structure of the crystallites, as is the case e.g. with zeolites which may be used according to this invention.

Preferred acid-binding metal salts are those containing no or strongly combined water of crystallisation, such as compounds that do not release any water when heated to 150° C., in particular to 200° C., under normal pressure in the air.

Compounds of the series of the hydrotalcites can be represented by the general formula IX $$M^{2+}{}_{1-x}.M^{3+}{}_x.(OH)_2.(A^{n-})_{x/n}.pH_2O \qquad \text{(IX),}$$

wherein $M^{2+}$=Mg, Ca, Sr, Ba, Zn, Pb, Sn and/or Ni, $M^{3+}$=Al, B or Bi, $A^n$ is an anion of valency n, n is a number from 1 to 4, x is a number from 0 to 0.5, p is a number from 0 to 2, and A=$OH^-$, $Cl^-$, $Br^-$, $I^-$, $ClO_4^-$, $HCO_3^-$, $CH_3COO^-$, $C_6H_5COO^-$, $CO_3^{2-}$, $SO_4^{2-}$,

$(CHOHCOO)_2{}^{2-}$, $(CHOH)_4CH_2OHCOO^-$, $C_2H_4(COO)_2{}^{2-}$, $(CH_2COO)_2{}^{2-}$, $CH_3CHOHCOO^-$, $SiO_3{}^{2-}$, $SiO_4{}^{4-}$, $Fe(CN)_6{}^{3-}$, $Fe(CN)_6{}^{4-}$, $BO_3{}^{3-}$, $PO_3{}^{3-}$ or $HPO_4{}^{2-}$.

Other hydrotalcites which may conveniently be used in the process described above are compounds of the general formula IXa, $$M_x{}^{2+}Al_2(OH)_{2x+6nz}(A^{n-})_2.pH_2O \qquad \text{(IXa),}$$

and $M^{2+}$ in this formula IXa is at least one metal of the series consisting of Mg and Zn, preferably Mg; $A^{n-}$ is an anion, typically of the series consisting of $CO_3{}^{2-}$,

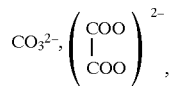

$OH^{31}$ and $S^{2-}$, and the anion has the valency n; p is a positive integer, preferably from 0.5 to 5; and x and z are positive integers, x preferably being from 2 to 6 and z being smaller than 2.

Preferred compounds are those of the series of the hydrotalcites of the general formula IX, $$M^{2+}_{1-x}\cdot M^{3+}_{x}\cdot(OH)_2\cdot(A^{n-})_{x/n}\cdot pH_2O \qquad (IX)$$

wherein $M^{2+}$ is Ca, Mg or a solid solution of Mg and Zn; $A^{n-}$ is $CO_3^{2-}$, $BO_3^{3-}$ or $PO_3^{3-}$; x is a number from 0 to 0.5, and p is a number from 0 to 2. Of these metal salts, those wherein $M^{3+}$ is an aluminium ion, are particularly preferred.

The use of basic hydrotalcites is preferred.

Very particularly preferred are hydrotalcites having the empirical formulae:

$$Al_2O_3\cdot 6MgO\cdot CO_2\cdot 12H_2O, \qquad (IXb)$$

$$Mg_{4.5}Al_2(OH)_{13}\cdot CO_3\cdot 3.5H_2O, \qquad (IXc)$$

$$4MgO\cdot Al_2O_3\cdot CO_2\cdot 9H_2O, \qquad (IXd)$$

$$4MgO\cdot Al_2O_3\cdot CO_2\cdot 6H_2O, \qquad (IXe)$$

$$ZnO\cdot 3MgO\cdot Al_2O_3\cdot CO_2\cdot 8-9H_2O \text{ or} \qquad (IXf)$$

$$ZnO\cdot 3MgO\cdot Al_2O_3\cdot CO_2\cdot 5-6H_2O. \qquad (IXg)$$

In the practice of this invention it is also possible to use zeolites of the general formula (X)

$$M_{x/n}[(AlO_2)_x(SiO_2)_y]\cdot wH_2O \quad (X),$$

wherein n is the charge of the cation M, and M is an element of the first or second main group, in particular Na, K, Mg and/or Ca, y:x is a number from 0.8 to 1.2, and w is a number from 0.5 to 10.

Basic zeolites are preferred.

Typical examples of suitable zeolites are compounds of the following empirical formulae:

$$Na_{12}[(AlO_2)_{12}(SiO_2)_{12}]\cdot 12H_2O$$

$$Ca_{4.5}Na_3[(AlO_2)_{12}(SiO_2)_{12}]\cdot 30H_2O$$

$$K_9Na_3[(AlO_2)_{12}(SiO_2)_{12}]\cdot 27H_2O$$

Basic metal salts, for example basic hydrotalcites or zeolites, will be taken to mean those compounds which induce a pH higher than 7 in water.

The carbonates, bicarbonates, hydroxides, phosphites and borates for use according to this invention are preferably magnesium carbonate, zirconium carbonate and calcium carbonate; sodium bicarbonate and potassium bicarbonate; magnesium hydroxide, calcium hydroxide, copper hydroxide, zinc hydroxide and aluminium hydroxide; secondary and tertiary sodium phosphite and potassium phosphite; and sodium borate and calcium borate.

It is also possible to use metal oxides in the practice of this invention. Oxides of divalent metals are preferred. Particularly preferred oxides are those of the metals of the second main or subsidiary group, in particular zinc oxide, calcium oxide and magnesium oxide.

Typical examples of metal carboxylates are the metal salts of saturated, unsaturated or hydroxylated aliphatic carboxylic acids. Particularly suitable are the salts of monocarboxylic acids of 6 to 20 carbon atoms, e.g. hexanoic acid, heptanoic acid, octanoic acid, 2-ethylhexanoic acid, undecanoic acid, lauric acid, myristic acid, palmitic acid, stearic acid, 12-oxystearic acid, oleic acid, linoleic acid or ricinolic acid, as well as the salts of dicarboxylic acids of 2 to 8 carbon atoms, such as oxalic acid, malonic acid, succinic acid, glutaric acid, adipic acid, pimelic acid, subaric acid, azelaic acid, sebacic acid, maleic acid, fumaric acid or tartaric acid. As salts of tricarboxylic acid, citrates also merit mention.

The metal salts of aromatic carboxylic acids, e.g. substituted benzoates or phthalates, are also of interest.

Metals of the series Ba, Sr, Ca, Mg and Zn are preferred. Preferred metal carboxylates are typically calcium stearate or zinc stearate and zinc oleate or calcium oleate.

The novel composition preferably comprises as amine (b) a sterically hindered amine or an amine of formula I

wherein $X_1$ and $X^2$ are each independently of the other H, $C_1$–$C_{20}$alkyl, $C_4$–$C_{20}$alkyl which is interrupted by —O— and optionally substituted by —OH, and wherein one or more than one ether group and, optionally, hydroxyl group, may be present, or are $C_2$–$C_{20}$hydroxyalkyl, and $X^3$ is $C_2$–$C_{20}$alkyl, $C_4$–$C_{20}$alkyl which is interrupted by —O— and optionally substituted by hydroxy, —$(CH_2)_m$—$NX^1X^2$, or $C_2$–$C_{20}$hydroxyalkyl; or wherein $X^2$ and $X^3$ taken together are $C_4$–$C_8$alkylene, or $C_3$–$C_{12}$alkylene which is interrupted by —O— or —$NX^1$, for example —$(CH_2)_m$—, —$C_2H_4$—O—$C_2H_4$— or —$C_2H_4$—$NX^1$—$C_2H_4$—, wherein m is an integer from 4 to 6, and $X^1$ and $X^2$ have the meanings indicated above; or an aromatic amine of formula Ia

wherein D is a nitrogen atom or a group —$CX^5$—, and $X^4$, $X^{4'}$, $X^{4''}$ and $X^5$ are each independently of one another hydrogen or $C_1$–$C_4$alkyl.

The sterically hindered amine is usually a cyclic sterically hindered amine, more particularly a compound of the series of the drivatives of polyalkylpiperidines or polyalkylpiperazines, comprising at least one group of formula II or III

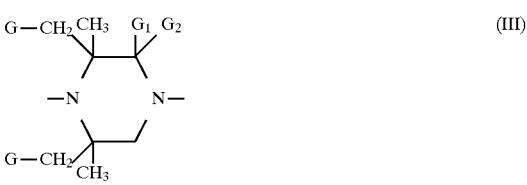

wherein G is hydrogen or methyl, and $G_1$ and $G_2$ are hydrogen, methyl or, taken together, are =O. The polyalkylpiperidine groups of formula II or III are preferably in 4-position and are substituted by one or two polar substituents or by a polar spiro ring system.

The use of a sterically hindered amine is preferred.

$X^1$, $X^2$ and $X^3$ each embrace, inter alia, ethyl, propyl, butyl, pentyl, hexyl, heptyl, octyl, nonyl, decyl, hydroxyethyl, hydroxypropyl, hydroxybutyl, hydroxypentyl, hydroxyhexyl, hydroxyheptyl, hydroxyoctyl, hydroxynonyl or hydroxydecyl. $X^1$, $X^2$ and $X^3$ are preferably identical.

The amine of formula I or Ia may typically be a tertiary amine, more preferably a tri-$C_2$–$C_4$alkanolamine such as triisopropanol amine (=amine A), or an aromatic amine such as trimethyltriazine, typically 1,3,5-trimethyl-2,4,6-triazine (=amine Z), or also a secondary amine such as dibutylamine, 2,2,6,6-tetramethylpiperidine (=amine X), 4-hydroxy-2,2,6,6-tetramethylpiperidine (HTMP;=amine Y) or piperazine.

An important process is that wherein the amine is a tertiary amine of formula I or Ia or a cyclic sterically hindered amine containing at least one group of formula II or III, wherein G is hydrogen and $G^1$ and $G^2$ are hydrogen or, taken together, are a substituent =O.

The use of derivatives of 2,2,6,6-tetramethylpiperidine in the novel process is particularly preferred.

The use of the classes of polyalkylpiperidines described hereinafter under (a) to (h) and carrying at least one group of formula II or III as indicated above, is of particular interest:

(a) compounds of formula IV

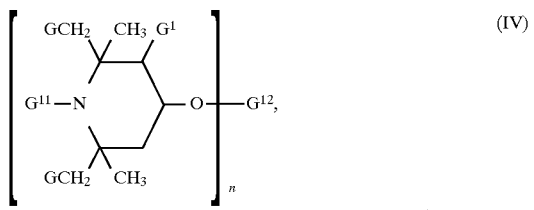

wherein n is a number from 1 to 4, G and $G^1$ are each independently of the other hydrogen or methyl,
$G^{11}$ is hydrogen, oxyl, hydroxyl, $C_1$–$C_{18}$alkyl, $C_3$–$C_8$alkenyl, $C_3$–$C_8$alkynyl, $C_7$–$C_{12}$aralkyl, $C_1$–$C_{18}$alkoxy, $C_5$–$C_8$cycloalkoxy, $C_7$–$C_9$phenylalkoxy, $C_1$–$C_8$alkanoyl, $C_3$–$C_5$alkenoyl,
$C_1$–$C_{18}$alkanoyloxy, benzyloxy, glycidyl or a group —$CH_2CH(OH)$—Z, wherein Z is
hydrogen, methyl or phenyl, and $G^{11}$ is preferably H, $C_1$–$C_4$alkyl, allyl, benzyl, acetyl or acryloyl, and $G^{12}$, if n=1, is hydrogen, $C_1$–$C_{18}$alkyl which may be interrupted by one or more than one oxygen atom, cyanoethyl, benzyl, glycidyl, a monovalent radical of an aliphatic, cycloaliphatic, araliphatic, unsaturated or aromatic carboxylic acid, carbaminic acid or phosphorus-containing acid, or a monovalent silyl radical, preferably a radical of an aliphatic carboxylic acid of 2 to 18 carbon atoms, of a cycloaliphatic carboxylic acid of 7 to 15 carbon atoms, of a α,β-unsaturated carboxylic acid of 3 to 5 carbon atoms, or of an aromatic carboxylic acid of 7 to 15 carbon atoms, and the carboxylic acid may be in each case substituted in the aliphatic, cycloaliphatic or aromatic moiety by 1 to 3 groups —$COOZ^{12}$, wherein $Z^{12}$ is H, $C_1$–$C_{20}$alkyl, $C_3$–$C_{12}$alkenyl, $C_5$–$C_7$cycloalkyl, phenyl or benzyl, if n=2, is $C_2$–$C_{12}$alkylene, $C_4$–$C_{12}$alkenylene, xylylene, a divalent radical of an aliphatic, cycloaliphatic, araliphatic or aromatic dicarboxylic acid, dicarbamic acid or phosphorus-containing acid, or a divalent silyl radical, preferably a radical of an aliphatic dicarboxylic acid of 2 to 36 carbon atoms, of a cycloaliphatic or aromatic dicarboxylic acid of 8 to 14 carbon atoms or of an aliphatic, cycloaliphatic or aromatic dicarbamic acid of 8 to 14 carbon atoms, and the dicarboxylic acid may be in each case substituted in the aliphatic, cycloaliphatic or aromatic moiety by 1 or 2 groups —$COOZ^{12}$,
  if n=3, is a trivalent radical of an aliphatic, cycloaliphatic or aromatic tricarboxylic acid, which radical can be substituted in the aliphatic, cycloaliphatic or aromatic moiety by —$COOZ^{12}$, or is a trivalent radical of an aromatic tricarbamic acid or of a phosphorus-containing acid, or is a trivalent sylil radical, and
  if n=4, is a tetravalent radical of an aliphatic, cycloaliphatic or aromatic tetracarboxylic acid.

The indicated carboxylic acid radicals in each case comprise radicals of formula (—CO)$_n$R, in which the meaning of n is as indicated above and the meaning of R follows from the given definition.

$C_1$–$C_{12}$Alkyl substituents are typically methyl, ethyl, n-propyl, n-butyl, sec-butyl, tert-butyl, n-hexyl, n-octyl, 2-ethylhexyl, n-nonyl, n-decyl, n-undecyl or n-dodecyl. $G^{11}$ or $G^{12}$ defined as $C_1$–$C_{18}$alkyl may typically be the groups indicated above and, in addition, e.g. n-tridecyl, n-tetradecyl, n-hexadecyl or n-octadecyl. $G^{11}$ defined as $C_3$–$C_8$alkenyl may be, for example, 1-propenyl, allyl, methallyl, 2-butenyl, 2-pentenyl, 2-hexenyl, 2-octenyl, 4-tert-butyl-2-butenyl.

$G^{11}$ defined as $C_3$–$C_8$alkynyl is preferably propargyl.

$G^{11}$ defined as $C_7$–$C_{12}$aralkyl is preferably phenethyl, more particularly benzyl.

$G^{11}$ defined as $C_1$–$C_8$alkanoyl is typically formyl, propionyl, butyryl, octanoyl, but preferably acetyl and, as $C_3$–$C_5$alkenoyl, is preferably acryloyl.

$G^{12}$ defined as a monovalent radical of a carboxylic acid is typically the radical of acetic acid, hexanoic acid, stearic acid, acrylic acid, methacrylic acid, benzoic acid or β(3,5-di-tert-butyl-4-hydroxy-phenyl)propionic acid.

$G^{12}$ defined as a monovalent silyl radical is typically a radical of formula —($C_jH_{2j}$)—Si(Z')$_2$Z", wherein j is an integer from 2 to 5, and Z' and Z" are each independently of the other $C_1$–$C_4$alkyl or $C_1$–$C_4$alkoxy.

$G^{12}$ defined as a divalent radical of a dicarboxylic acid is typically the radical of malonic acid, succinic acid, glutaric acid, adipic acid, subaric acid, sebacic acid, maleic acid, itaconic acid, phthalic acid, dibutylmalonic acid, dibenzylmalonic acid, butyl(3,5-di-tert-butyl-4-hydroxybenzyl) malonic acid or bicycloheptenedicarboxylic acid.

$G^{12}$ defined as a trivalent radical of a tricarboxylic acid is typically the radical of trimellitic acid, citric acid or nitrilotriacetic acid.

$G^{12}$ defined as a tetravalent radical of a tetracarboxylic acid is typically the tetravalent radical of butane-1,2,3,4-tetracarboxylic acid or of pyromellitic acid.

$G^{12}$ defined as a divalent radical of a dicarbamic acid is typically a hexamethylene-dicarbamic acid radical or a 2,4-toluylenedicarbamic acid radical.

Preferred compounds are those of formula IV, wherein G is hydrogen, $G^{11}$ is hydrogen or methyl, n is 2, and $G^{12}$ is the diacyl radical of an aliphatic dicarboxylic acid of 4 to 12 carbon atoms.

Illustrative examples of polyalkylpiperidine compounds of this class are:

1) 4-hydroxy-2,2,6,6-tetramethylpiperidine
2) 1-allyl-4-hydroxy-2,2,6,6-tetramethylpiperidine
3) 1-benzyl-4-hydroxy-2,2,6,6-tetramethylpiperidine
4) 1-(4-tert-butyl-2-butenyl)-4-hydroxy-2,2,6,6-tetramethylpiperidine
5) 4-stearoyloxy-2,2,6,6-tetramethylpiperidine
6) 1-ethyl-4-salicyloyloxy-2,2,6,6-tetramethylpiperidine
7) 4-methacryloyloxy-1,2,2,6,6-pentamethylpiperidine
8) 1,2,2,6,6-pentamethylpiperidine-4-yl-β(3,5-di-tert-butyl-4-hydroxyphenyl)propionate
9) bis(1-benzyl-2,2,6,6-tetramethylpiperidin-4-yl) maleinate
10) bis(2,2,6,6-tetramethylpiperidin-4-yl)succinate 11) bis(2,2,6,6-tetramethylpiperidin-4-yl)glutarate
12) bis(2,2,6,6-tetramethylpiperidin-4-yl)adipate
13) bis(2,2,6,6-tetramethylpiperidin-4-yl)sebacate
14) bis(1,2,2,6,6-pentamethylpiperidin-4-yl)sebacate
15) bis(1,2,3,6-tetramethyl-2,6-diethyl-piperidin-4-yl)sebacate
16) bis(1-allyl-2,2,6,6-tetramethylpiperidin-4-yl)phthalate
17) 1-hydroxy-4-β-cyanoethyloxy-2,2,6,6-tetramethylpiperidine
18) 1-acetyl-2,2,6,6-tetramethylpiperidin-4-yl-acetate
19) the tris(2,2,6,6-tetramethylpiperidin-4-yl) ester of trimellitic acid
20) 1-acryloyl-4-benzyloxy-2,2,6,6-tetramethylpiperidine
21) the bis(2,2,6,6-tetramethylpiperidin-4-yl) ester of diethylmalonic acid
22) the bis(1,2,2,6,6-pentamethylpiperidin-4-yl) ester of dibutylmalonic acid
23) the bis(1,2,2,6,6-pentamethylpiperidin-4-yI) ester of butyl(3,5-di-tert-butyl-4-hydroxybenzyl)malonic acid
24) bis(1-octyloxy-2,2,6,6-tetramethylpiperidin-4-yl)sebacate
25) bis(1-cyclohexyloxy-2,2,6,6-tetramethylpiperidin-4-yl)sebacate
26) hexane-1',6'-bis(4-carbamoyloxy-1-n-butyl-2,2,6,6-tetramethyl-piperidine)
27) toluene-2',4'-bis(4-carbamoyloxy-1-n-propyl-2,2,6,6-tetramethyl-piperidine)
28) dimethyl-bis(2,2,6,6-tetramethylpiperidin-4-oxy)silane
29) phenyl-tris(2,2,6,6-tetramethylpiperidin-4-oxy)silane
30) tris(1-propyl-2,2,6,6-tetramethylpiperidin-4-yl)phosphite
31) tris(1-propyl-2,2,6,6-tetramethylpiperidin-4-yl)phosphate
32) phenyl-[bis(1,2,2,6,6-pentamethylpiperidin-4-yl)]phosphonate
33) 4-hydroxy-1,2,2,6,6-pentamethylpiperidine
34) 4-hydroxy-N-hydroxyethyl-2,2,6,6-tetramethylpiperidine
35) 4-hydroxy-N(2-hydroxypropyl)-2,2,6,6-tetramethylpiperidine
36) 1-glycidyl-4-hydroxy-2,2,6,6-tetramethylpiperidine (b) compounds of formula (V)

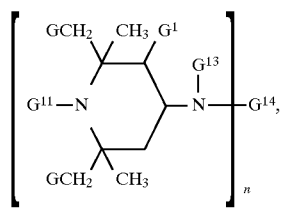

(V)

wherein n is 1 or 2, and G, $G^1$ and $G^{11}$ have the meaning given in (a), $G^{13}$ is hydrogen, $C_1$–$C_{12}$alkyl, $C_2$–$C_5$hydroxyalkyl, $C_5$–$C_7$cycloalkyl, $C_7$–$C_8$aralkyl, $C_2$–$C_{18}$alkanoyl, $C_3$–$C_5$alkenoyl, benzoyl or a group of formula

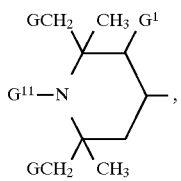

and $G^{14}$, if n=1, is hydrogen, $C_1$–$C_{18}$alkyl, $C_3$–$C_8$alkenyl, $C_5$–$C_7$cycloalkyl; $C_1$–$C_4$alkyl which is substituted by a hydroxy, cyano, alkoxycarbonyl or carbamide group; glycidyl; a group of formula —$CH_2$—CH(OH)—Z or of formula —CONH—Z, wherein Z is hydrogen, methyl or phenyl;

if n=2, is $C_2$–$C_{12}$alkylene, $C_6$–$C_{12}$arylene, xylylene, a —$CH_2$—CH(OH)—$CH_2$— group or a group —$CH_2$—CH(OH)—$CH_2$—O—D—O—, wherein D is $C_2$–$C_{10}$alkylene, $C_6$–$C_{15}$arylene, $C_6$–$C_{12}$cycloalkylene; or, provided that $G^{13}$ is not alkanoyl, alkenoyl or benzoyl, $G^{14}$ may also be 1-oxo-$C_2$–$C_{12}$alkylene, a divalent radical of an aliphatic, cycloaliphatic or aromatic dicarboxylic acid or dicarbamic acid, or also the group —CO—; or if n=1, $G^{13}$ and $G^{14}$, taken together, may be the divalent radical of an aliphatic, cycloaliphatic or aromatic 1,2-dicarboxylic acid or 1,3-dicarboxylic acid.

$C_1$–$C_{12}$Alkyl substituents or $C_1$–$C_{18}$alkyl substituents have the meaning indicated under (a).

$C_5$–$C_7$Cycloalkyl substituents are preferably cyclohexyl.

$G^{13}$ defined as $C_7$–$C_8$aralkyl is preferably phenylethyl or, more particularly, benzyl. $G^{13}$ defined as $C_2$–$C_5$hydroxyalkyl is preferably 2-hydroxyethyl or 2-hydroxypropyl.

$G^{13}$ defined as $C_2$–$C_{18}$alkanoyl is typically propionyl, butyryl, octanoyl, dodecanoyl, hexadecanoyl, octadecanoyl, but preferably acetyl and, as $C_3$–$C_5$alkenoyl, is preferably acryloyl.

$G^{14}$ defined as $C_2$–$C_8$alkenyl is typically allyl, methallyl, 2-butenyl, 2-pentenyl, 2-hexenyl or 2-octenyl.

$G^{14}$ defined as $C_1$–$C_4$alkyl which is substituted by a hydroxy, cyano, alkoxycarbonyl or carbamide group may typically be 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl)ethyl.

$C_2$–$C12$Alkylene substituents are typically ethylene, propylene, 2,2-dimethylpropylene, tetramethylene, hexamethylene, octamethylene, decamethylene or dodecamethylene.

$C_6$–$C_{15}$Arylene substituents are typically o-, m- or p-phenylene, 1,4-naphthylene or 4,4'-diphenylene.

$C_6$–$C_{12}$Cycloalkylene is preferably cyclohexylene.

Preferred compounds are those of formula V, wherein n is 1 or 2, G is hydrogen, $G^{11}$ is hydrogen or methyl, $G^{13}$ is hydrogen, $C_1$–$C_{12}$alkyl or a group of formula

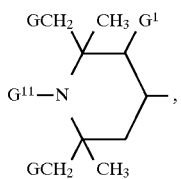

and, if n=1, $G^{14}$ is hydrogen or $C_1$–$C_{12}$alkyl and, if n=2, is $C_2$–$C_8$alkylene or 1-oxo-$C_2$–$C_8$alkylene.

Illustrative examples of polyalkylpiperidine compounds of this class are:

37) N,N'-bis(2,2,6,6-tetramethylpiperidin-4-yl) hexamethylene-1,6-diamine
38) N,N'-bis(2,2,6,6-tetramethylpiperidin-4-yl) hexamethylene-1,6-diacetamide
39) bis(2,2,6,6-tetramethylpiperidin-4-yl)amine
40) 4-benzoylamino-2,2,6,6-tetramethylpiperidine
41) N,N'-bis(2,2,6,6-tetramethylpiperidin-4-yl)-N,N'-dibutyladipamide
42) N,N'-bis(2,2,6,6-tetramethylpiperidin-4-yl)-N,N'-dicyclohexyl-2-hydroxypropylene-1,3-diamine
43) N,N'-bis(2,2,6,6-tetramethylpiperidin-4-yl)-p-xylylenediamine
44) N,N'-bis(2,2,6,6-tetramethylpiperidin-4-yl) succindiamide
45) the bis(2,2,6,6-tetramethylpiperidin-4-yl) ester of N-(2,2,6,6-tetramethylpiperidin-4-yl)-β-aminodipropionic acid
46) the compound of formula

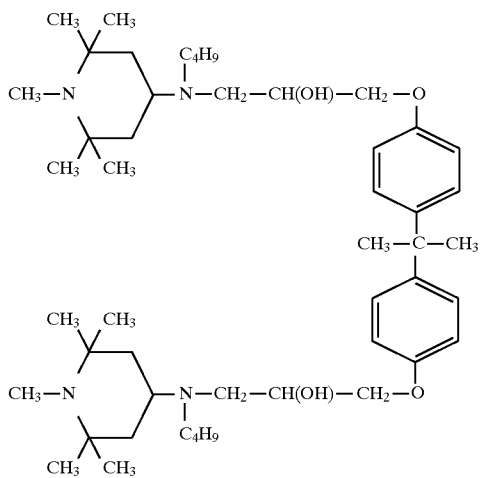

47) 4-(bis-2-hydroxyethylamino)-1,2,2,6,6-pentamethylpiperidine
48) 4-(3-methyl-4-hydroxy-5-tert-butylbenzoic acid amido)-2,2,6,6-tetramethylpiperidine
49) 4-methacrylamido-1,2,2,6,6-pentamethylpiperidine (c) compounds of formula (VI)

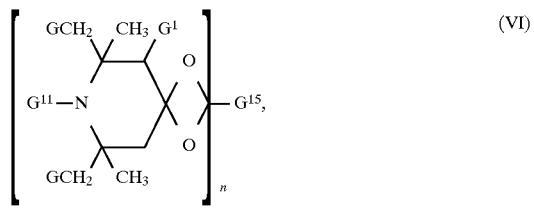

wherein n is 1 or 2, and G, $G^1$ and $G^{11}$ have the meaning indicated under (a), and $G^{15}$, if n=1, is $C_2$–$C_8$alkylene, $C_2$–$C_8$hydroxyalkylene or $C_4$–$C_{22}$acyloxyalkylene; if n=2, is the group $(-CH_2)_2C(CH_2-)_2$.

$G^{15}$ defined as $C_2$–$C_8$alkylene or $C_2$–$C_8$hydroxyalkylene is typically ethylene, 1-methylethylene, propylene, 2-ethylpropylene or 2-ethyl-2-hydroxymethylpropylene.

$G^{15}$ defined as $C_4$–$C_{22}$acyloxyalkylene is typically 2-ethyl-2-acetoxymethylpropylene.

Illustrative examples of polyalkylpiperidine compounds of this class are:

50) 9-aza-8,8,10,10-tetramethyl-1,5-dioxaspiro[5.5] undecane
51) 9-aza-8,8,10,10-tetramethyl-3-ethyl-1,5-dioxaspiro [5.5]undecane
52) 8-aza-2,7,7,8,9,9-hexamethyl-1,4-dioxaspiro[4.5] decane
53) 9-aza-3-hydroxymethyl-3-ethyl-8,8,9,10,10-pentamethyl-1,5-dioxaspiro[5.5]undecane
54) 9-aza-3-ethyl-3-acetoxymethyl-9-acetyl-8,8,10,10-tetramethyl-1,5-dioxaspiro[5.5]-undecane
55) 2,2,6,6-tetramethylpiperidine-4-spiro-2'-(1',3'-dioxane)-5'-spiro-5''-(1'',3''-dioxane)-2''-spiro-4'''-(2''',2''',6''',6'''-tetramethylpiperidine);

(d) compounds of formulae VIIA, VIIB and VIIC, preferably compounds of formula VIIC,

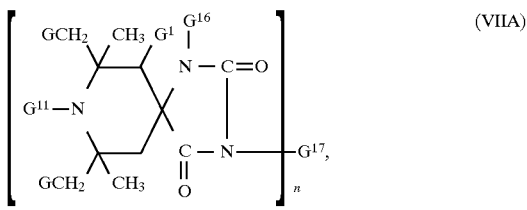

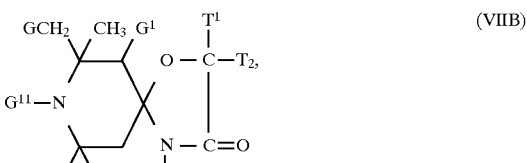

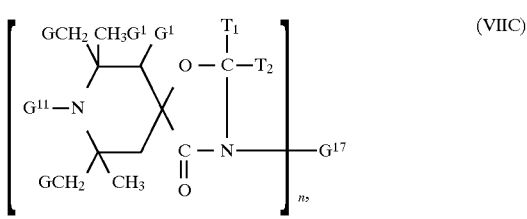

wherein n is 1 or 2, and G, $G^1$ and $G^{11}$ have the meaning indicated in (a), $G^{16}$ is hydrogen, $C_1$–$C_{12}$alkyl, allyl, benzyl, glycidyl or $C_2$–$C_6$alkoxyalkyl, and $G^{17}$, if n=1, is hydrogen, $C_1$–$C_2$alkyl, $C_3$–$C_5$alkenyl, $C_7$–$C_9$aralkyl, $C_5$–$C_7$cycloalkyl $C_2$–$C_4$hydroxyalkyl, $C_2$–$C_6$alkoxyalkyl, $C_6$–$C_{10}$aryl, glycidyl, or a group of formula $-(CH_2)p-COO-Q$ or of formula $-(CH_2)p-O-CO-Q$, wherein p is 1 or 2, and Q is $C_1$–$C_4$alkyl or phenyl; if n=2, is $C_2$–$C_{12}$alkylene, $C_4$–$C_{12}$alkenylene, $C_6$–$C_{12}$arylene, a group $-CH_2-CH(OH)-CH_2-O-D-O-CH_2-CH(OH)-CH_2-$, wherein D is $C_2$–$C_{10}$alkylene, $C_6$–$C_{15}$arylene, $C_6$–$C_{12}$cycloalkylene, or a group $-CH_2CH(OZ')CH_2-(OCH_2-CH(OZ')CH_2)_2-$, wherein Z' is hydrogen, $C_1$–$C_{18}$alkyl, allyl, benzyl, $C_2$–$C_{12}$alkanoyl or benzoyl, $T_1$ and $T_2$ are each independently of the other hydrogen, $C_1$–$C_{18}$alkyl or $C_6$–$C_{10}$aryl or $C_7$–$C_9$aralkyl each of which may be substituted by halogen or $C_1$–$C_4$alkyl, or $T_1$ and $T_2$, together with the linking carbon atom, form a $C_5$–$C_{14}$cycloalkane ring.

Substituents $C_1$–$C_{12}$alkyl are typically methyl, ethyl, n-propyl, n-butyl, sec-butyl, tert-butyl, n-hexyl, n-octyl, 2-ethylhexyl, n-nonyl, n-decyl, n-undecyl or n-dodecyl.

Substituents defined as $C_1$–$C_{18}$alkyl may typically be the groups indicated above and also e.g. n-tridecyl, n-tetradecyl, n-hexadecyl or n-octadecyl.

Substituents $C_2$–$C_6$alkoxyalkyl are typically methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

$G^{17}$ defined as $C_3$–$C_5$alkenyl is typically 1-propenyl, allyl, methallyl, 2-butenyl or 2-pentenyl.

$G^{17}$, $T_1$ and $T_2$ defined as $C_7$–$C_9$aralkyl are preferably phenethyl or, more particularly, benzyl. If $T_1$ and $T_2$, together with the carbon atom, form a cycloalkane ring, then said ring may typically be a cyclopentane, cyclohexane, cyclooctane or cyclododecane ring.

$G^{17}$ defined as $C_2$–$C_4$hydroxyalkyl is typically 2-hydroxyethyl, 2-hydroxypropyl, 2-hydroxybutyl or 4-hydroxybutyl.

$G^{17}$, $T_1$ and $T_2$ defined as $C_6$–$C_{10}$aryl is preferably phenyl, α- or β-naphthyl, each of which may be substituted by halogen or $C_1$–$C_4$alkyl.

$G^{17}$ defined as $C_2$–$C_{12}$alkylene is typically ethylene, propylene, 2,2-dimethylpropylene, tetramethylene, hexamethylene, octamethylene, decamethylene or dodecamethylene.

$G^{17}$ defined as $C_4$–$C_{12}$alkenylene is preferably 2-butenylene, 2-pentenylene or 3-hexenylene.

$G^{17}$ defined as $C_6$–$C_{12}$arylene is typically o-, m- or p-phenylene, 1,4-naphthylene or 4,4'-diphenylene.

Z' defined as $C_2$–$C_{12}$alkanoyl is typically propionyl, butyryl, octanoyl, dodecanoyl, but is preferably acetyl.

D defined as $C_2$–$C_{10}$alkylene, $C_6$–$C_{15}$arylene or $C_6$–$C_{12}$cycloalkylene is as defined under (b).

Illustrative examples of polyalkylpiperidine compounds of this class are:

56) 3-benzyl-1,3,8-triaza-7,7,9,9-tetramethylspiro[4.5]decane-2,4-dione
57) 3-n-octyl-1,3,8-triaza-7,7,9,9-tetramethylspiro[4.5]decane-2,4-dione
58) 3-allyl-1,3,8-triaza-1,7,7,9,9-pentamethylspiro[4.5]decane-2,4-dione
59) 3-glycidyl-1,3,8-triaza-7,7,8,9,9-pentamethylspiro[4.5]decane-2,4-dione
60) 1,3,7,7,8,9,9-heptamethyl-1,3,8-triazaspiro[4.5]decane-2,4-dione
61) 2-isopropyl-7,7,9,9-tetramethyl-1-oxa-3,8-diaza-4-oxo-spiro-[4.5]decane
62) 2,2-dibutyl-7,7,9,9-tetramethyl-1-oxa-3,8-diaza-4-oxo-spiro-[4.5]decane
63) 2,2,4,4-tetramethyl-7-oxa-3,20-diaza-21-oxo-dispiro[5.1.11.2]heneicosane
64) 2-butyl-7,7,9,9-tetramethyl-1-oxa-4,8-diaza-3-oxo-spiro-[4.5]decane and, preferably:

65) 8-acetyl-3-dodecyl-1,3,8-triaza-7,7,9,9-tetramethylspiro[4.5]decane-2,4-dione or the compounds of the following formulae:

66) 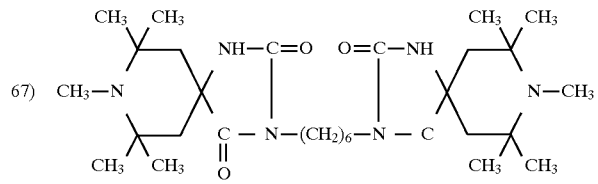

67) 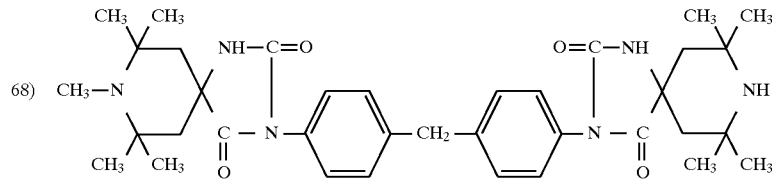

68) 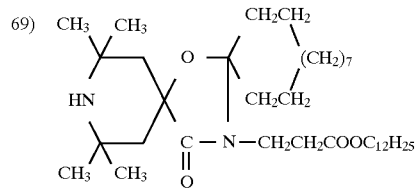

69) 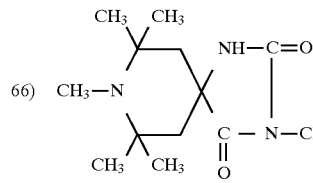

(e) compounds of formula VIII, which are likewise preferred,

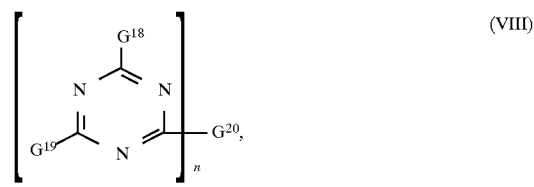

(VIII)

wherein n is 1 or 2, and $G^{18}$ is a group of one of formula

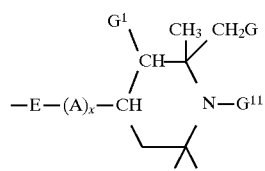

or

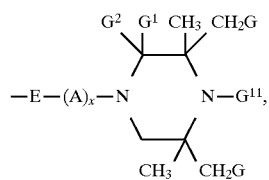

wherein G and $G^{11}$ are as defined in (a), and $G^1$ and $G^2$ are hydrogen, methyl or, taken together, are a substituent=O, E is —O— or —$NG^{13}$—, A is $C_2$–$C_6$alkylene or —$(CH_2)_3$—O—, and x is either 0 or 1, $G^{13}$ is hydrogen, $C_1$–$C_{12}$alkyl, $C_2$–$C_5$hydroxyalkyl or $C_5$–$C_7$cycloalkyl, $G^{19}$ is identical to $G^{18}$ or is one of the groups —$NG^{21}G^{22}$, —$OG^{23}$, —$NHCH_2OG^{23}$ or —$N(CH_2OG^{23})_2$, $G^{20}$, if n=1, is identical to $G^{18}$ or $G^{19}$, and, if n=2, is a group —E—B—E—, wherein B is $C_2$–$C_8$ alkylene or $C_2$–$C_8$alkylene which is interrupted by 1 or 2 groups —$N(G^{21})$—, $G^{21}$ is $C_1$–$C_{12}$alkyl, cyclohexyl, benzyl or $C_1$–$C_4$hydroxyalkyl, or a group of formula

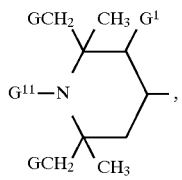

$G^{22}$ is $C_1$–$C_{12}$-alkyl, cyclohexyl, benzyl, $C_1$–$C_4$-hydroxyalkyl, and $G^{23}$ is hydrogen, $C_1$–$C_{12}$alkyl or phenyl, or $G^{21}$ and $G^{22}$, taken together, are $C_4$–$C_5$alkylene or $C_4$–$C_5$oxaalkylene, typically

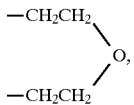

or a group of formula

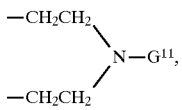

or $G^{21}$ is a group of formula

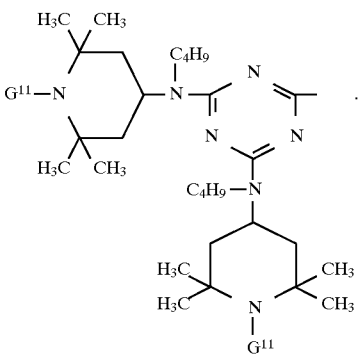

$C_1$–$C_{12}$Alkyl substituents are typically methyl, ethyl, n-propyl, n-butyl, sec-butyl, tert-butyl, n-hexyl, n-octyl, 2-ethylhexyl, n-nonyl, n-decyl, n-undecyl or n-dodecyl.

$C_1$–$C_4$Hydroxyalkyl substituents are typically 2-hydroxyethyl, 2-hydroxypropyl, 3-hydroxypropyl, 2-hydroxybutyl or 4-hydroxybutyl.

A defined as $C_2$–$C_6$alkylene is typically ethylene, propylene, 2,2-dimethylpropylene, tetramethylene or hexamethylene.

$G^{21}$ and $G^{22}$ together defined as $C_4$–$C_5$alkylene or oxaalkylene are typically tetramethylene, pentamethylene or 3-oxapentamethylene.

Illustrative examples of polyalkylpiperidine compounds of this class are compounds of the following formulae:

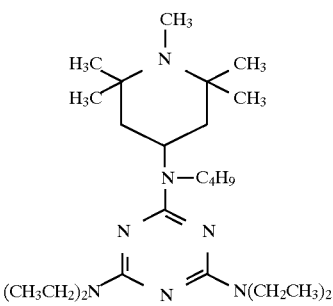

70)

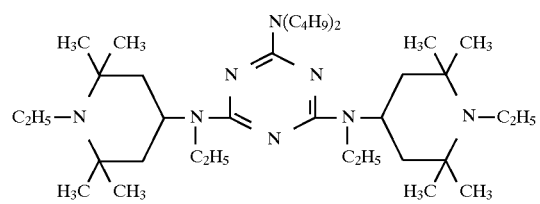

71)

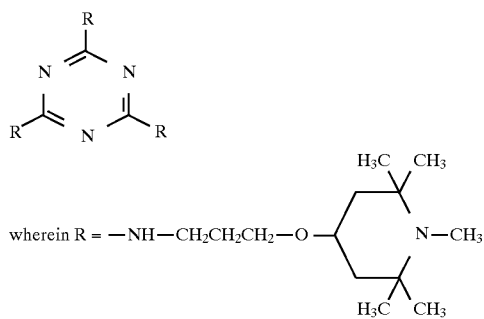
72)
wherein R = —NH—CH₂CH₂CH₂—O—[piperidine]
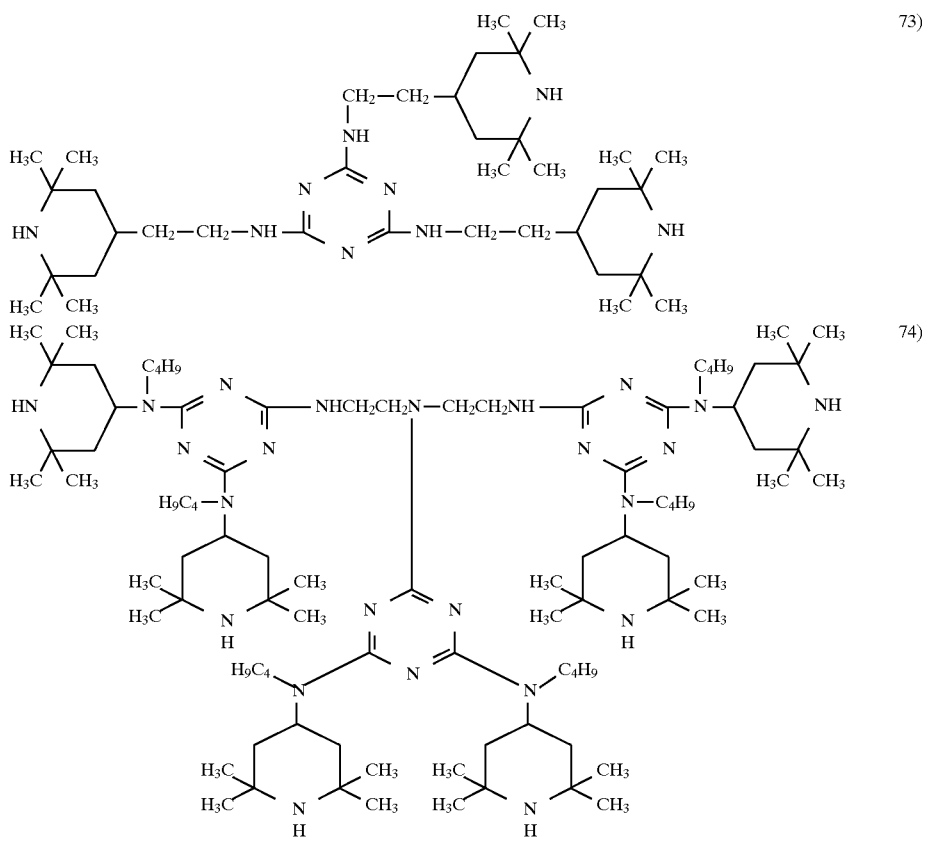
73)
74)
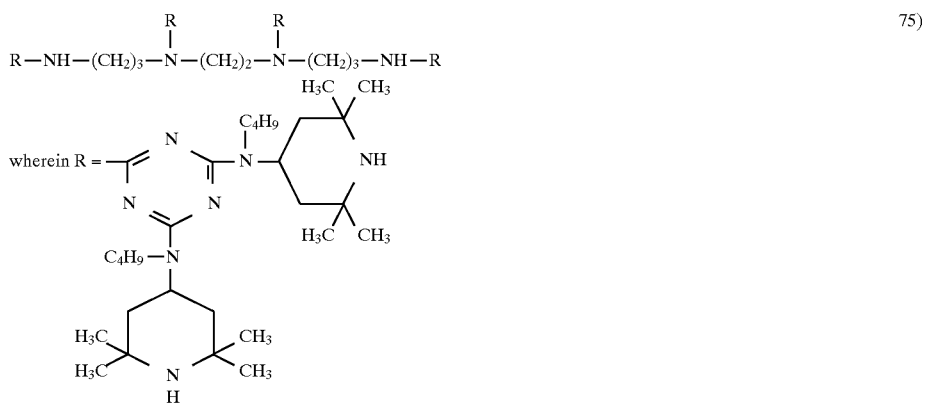
75)
wherein R =
$R-NH-(CH_2)_3-N(R)-(CH_2)_2-N(R)-(CH_2)_3-NH-R$  (amine J)  76)

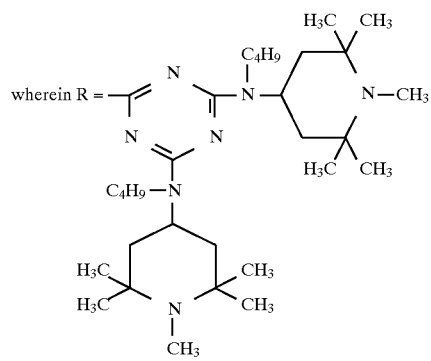
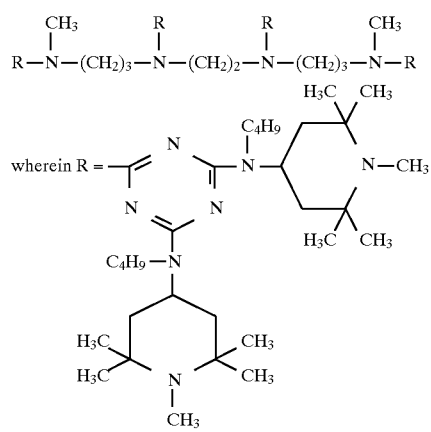
77)
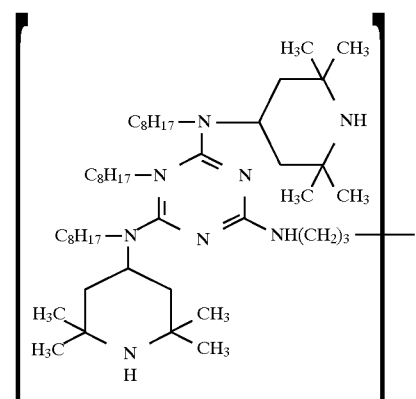
78)
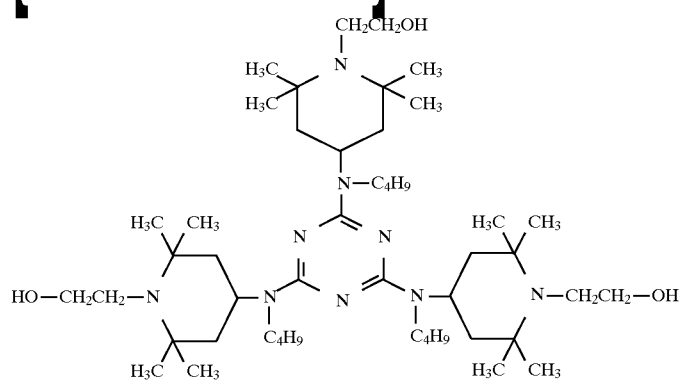
79)

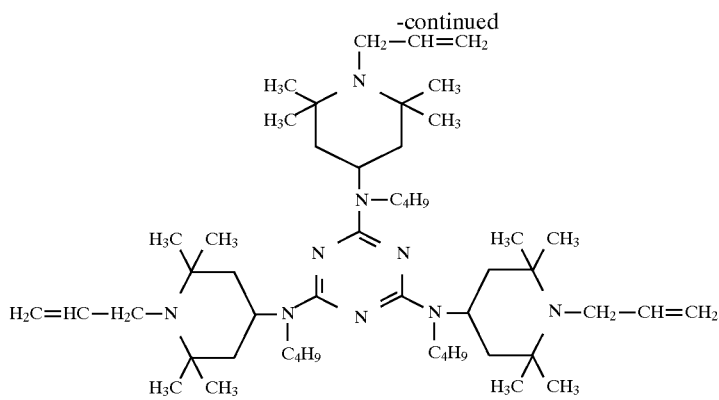
(80)

(f) oligomeric or polymeric compounds, whose structural repeating unit contains a 2,2,6,6-tetraalkylpiperidine radical of formula III, preferably polyesters, polyethers, polyamides, polyamines, polyurethanes, polyureas, polyaminotriazines, poly(meth)acrylates, poly(meth)acrylamides and the copolymers thereof containing such radicals.

Typical examples of 2,2,6,6-polyalkylpiperidine light stabilisers of this class are the compounds of the following formulae, wherein m is a number from 2 to c. 200.

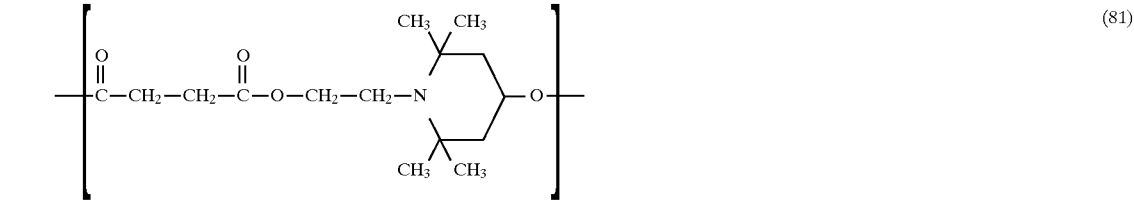
(81)

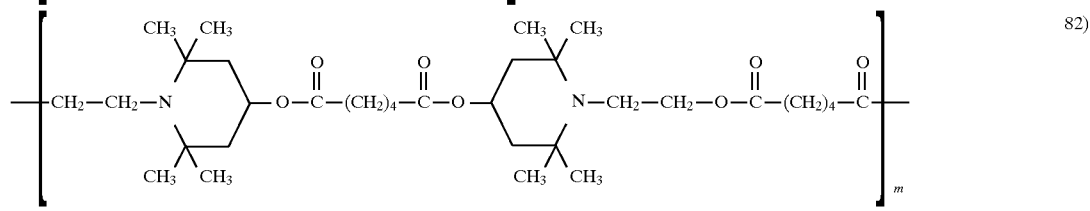
(82)

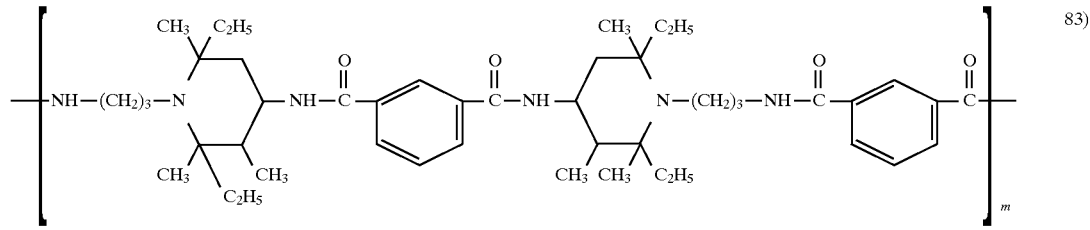
(83)

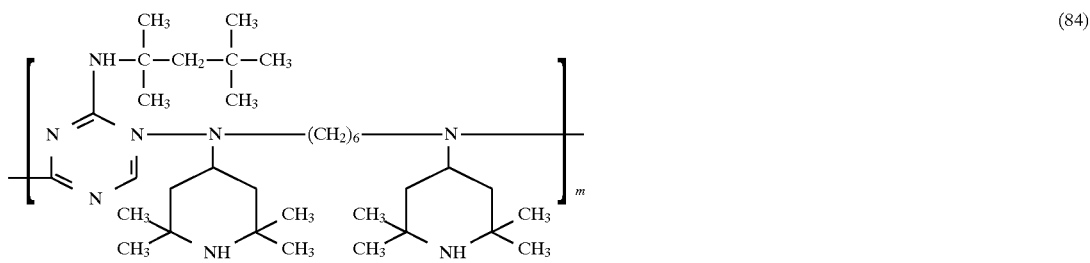
(84)

(85)

-continued
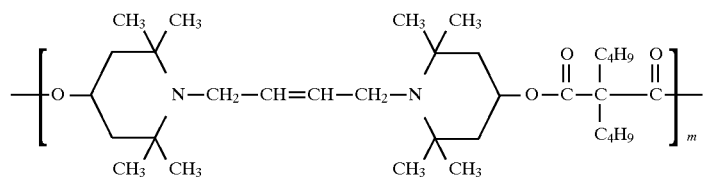 (86)
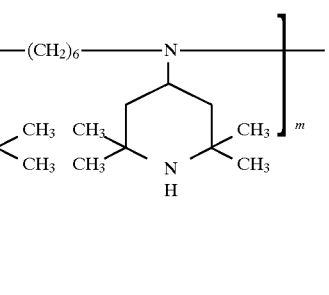 (87)
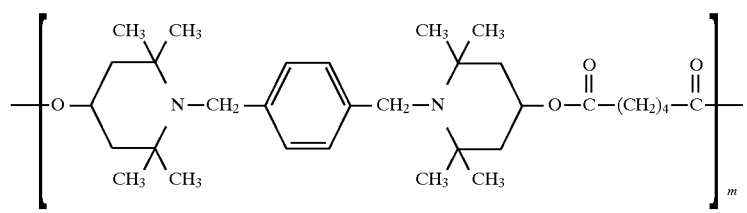 (88)
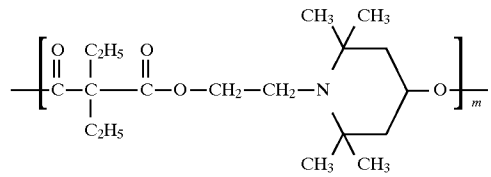 (89)
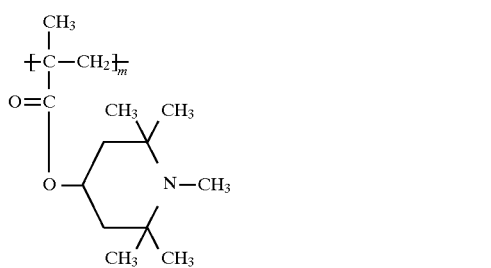 90)
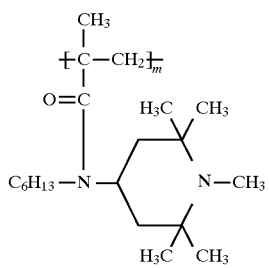 91)

-continued
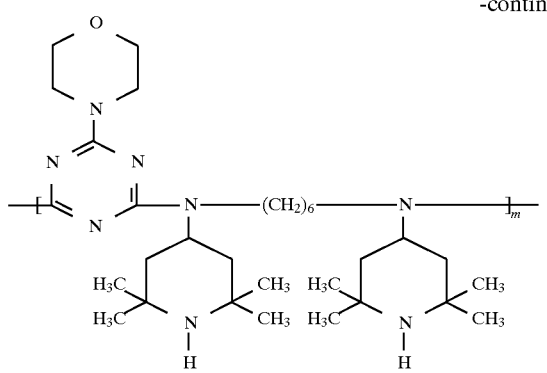
92)
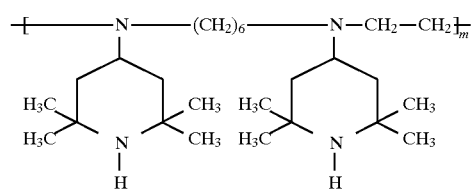
93)
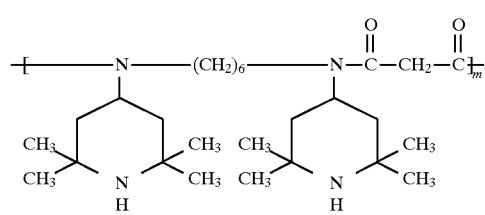
94)
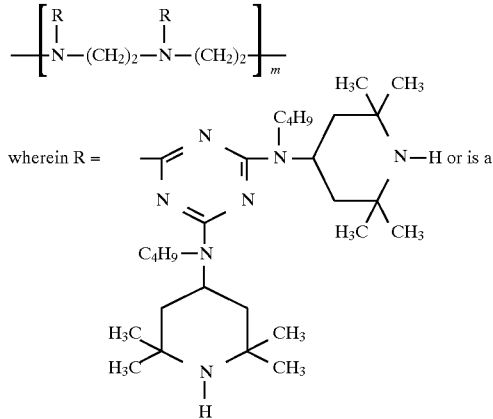
95)
branching of the chain
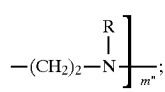
m' and m" are each an integer from 0 to 200, with the proviso that m'+m"=m.
Further illustrative examples of polymeric light stabilisers are reaction products of compounds of formula
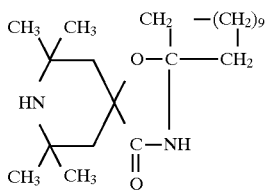
with epichlorohydrin;
polyester of butane-1,2,3,4-tetracarboxylic acid with a bifunctional alcohol of formula

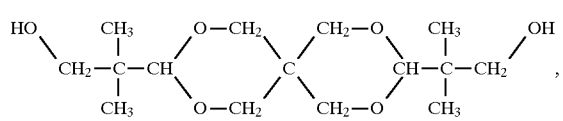

whose carboxyl side chains deriving from the tetracarboxylic acid are esterified with 2,2,6,6-tetramethyl-4-hydroxy-piperidine;

compounds of formula

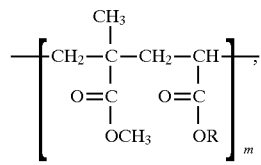

wherein about one third of the radicals R are —$C_2H_5$ and the others are

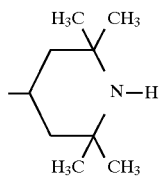

and m is a number from 2 to 200; or copolymers, whose structural repeating unit is composed of 2 units of

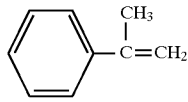

and 1 unit each of

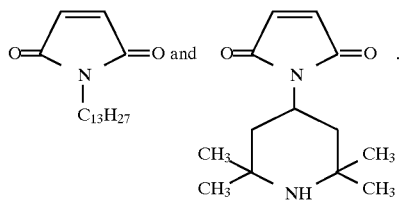

(g) Compounds of formula IX

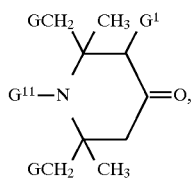
(IX)

wherein G, $G^1$ and $G^{11}$ are as defined under (a).
Preferred compounds are those of formula IX, wherein G is hydrogen or methyl, and $G^{11}$ is hydrogen or methyl.
Illustrative examples of such compounds are:
96) 2,2,6,6-tetramethyl-4-piperidone (triacetonamine)
97) 1,2,2,6,6-pentamethyl-4-piperidone
98) 2,2,6,6-tetramethyl-4-piperidon-1-oxyl
99) 2,3,6-trimethyl-2,6-diethyl-4-piperidone (h) Compounds of formula X

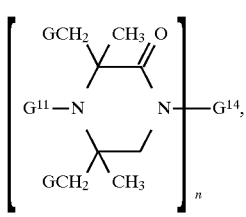
(X)

wherein n is 1 or 2, and G and $G^{11}$ are as defined under (a), and $G^{14}$ is as defined under (b), and $G^{14}$ cannot have the meanings —CONH—Z and —$CH_2$—CH(OH)—$CH_2$—O—D—O—.

Typical examples of such compounds are:

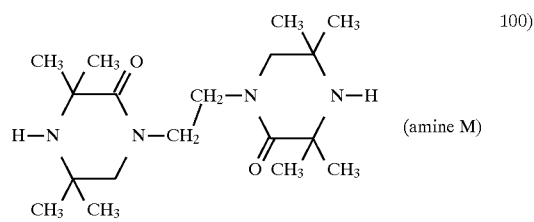

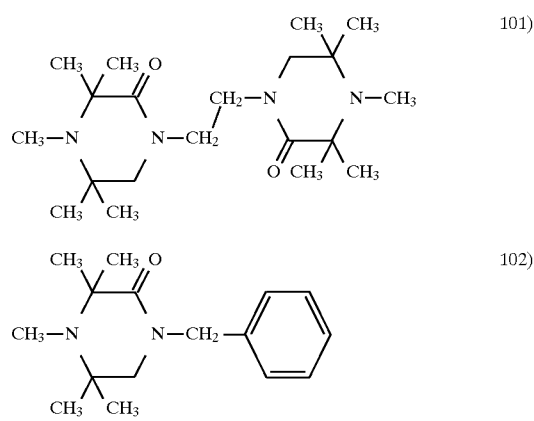

The following amines are particularly preferred for use in the novel process:

Compounds of formula IV, wherein n is an integer from 1 to 4, G and $G^1$ are hydrogen, and $G^{11}$ is hydrogen or $C_1$–$C_{18}$-alkyl, and $G^{12}$, if n=1, is a radical of formula—$(C_jH_{2j})$—$Si(Z')_2Z''$, wherein j is an integer from 2 to 5, and Z' and Z'' are each independently of the other $C_1$–$C_4$alkyl or $C_1$–$C_4$alkoxy, and $G^{12}$, if n=2, is a radical of an aliphatic dicarboxylic acid of 2 to 12 carbon atoms, which radical may be substituted by —$COOZ^{12}$, wherein $Z^{12}$ is $C_1$–$C_{20}$alkyl, $G^{12}$, if n=3, is a radical of an aromatic tricarboxylic acid of 9 to 15 carbon atoms, $G^{12}$, if n=4, is a radical of an aliphatic tetracarboxylic acid of 8 to 12 carbon atoms;

particularly interesting amines of this class are those of formulae

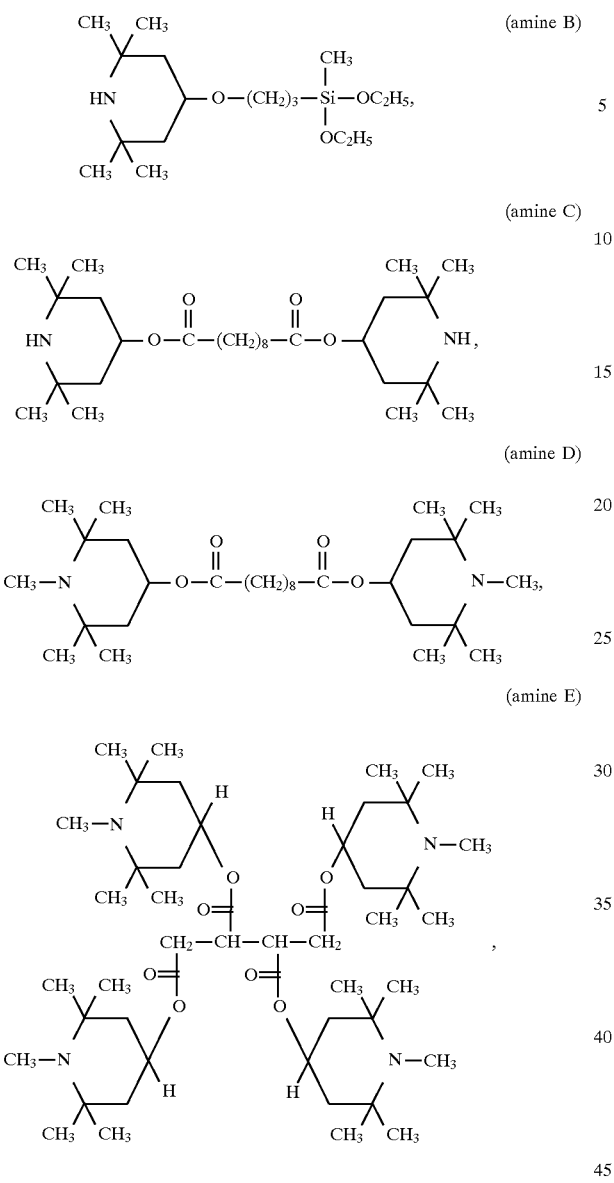

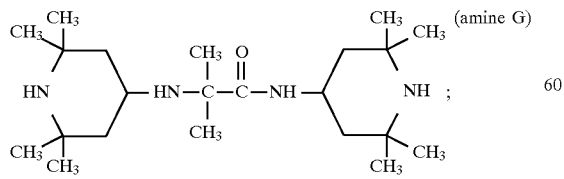

as well as esters of butane-1,2,3,4-tetracarboxylic acid containing 2 units each of 1,2,2,6,6-pentamethyl-4-hydroxypiperidine and $C_{13}H_{27}$—OH (amine F);

compounds of formula V, wherein n=2, G and $G^1$ are hydrogen,
$G^{11}$ is hydrogen or methyl, and
$G^{13}$ is hydrogen or $C_1$–$C_8$alkyl, and
$G^{14}$ is $C_2$–$C_8$alkylene or 1-oxo-$C_2$–$C_8$alkylene; a particularly interesting amine of this class is the compound of formula compounds of formula VIIC, wherein n=1, G, $G^1$ and $G^{17}$ are hydrogen,
$G^{11}$ is hydrogen or methyl, and
$T_1$ and $T_2$, together with the linking nitrogen atom, form a $C_5$–$C_{14}$cycloalkane ring; a particularly interesting amine of this class is the compound of formula

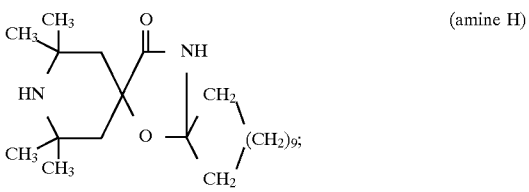

compounds of formula VIII, wherein n is 1 or 2,
$G^{18}$ and $G^{19}$ are a group of one of formula

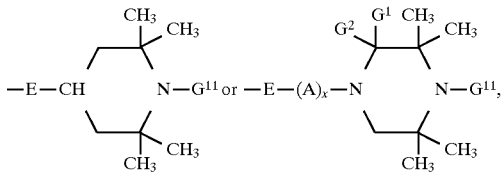

$G^{11}$ is hydrogen or methyl,
$G^1$ and $G^2$ are hydrogen or, taken together, are a substituent =O,
E is —O— or —NG$^{13}$—, A is $C_2$–$C_6$alkylene, and x is either 0 or 1,
$G^{13}$ is hydrogen, $C_1$–$C_{12}$alkyl or cyclohexyl,
$G^{20}$, if n=1, has the meaning of $G^{18}$ and, if n=2, is a group —E—B—E—, wherein B is $C_2$–$C_8$alkylene, or $C_2$–$C_8$alkylene which is interrupted by 1 or 2 groups —N($G^{21}$)—,
$G^{21}$ is $C_1$–$C_{12}$alkyl, cyclohexyl, benzyl or $C_1$–$C_4$hydroxyalkyl, or a group of formula

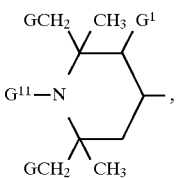

or $G^{21}$ is a group of formula

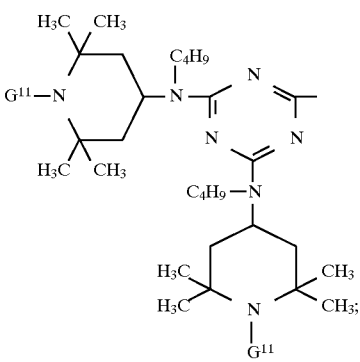

particularly interesting amines of this class are the compound (76)[=amine J] described above and the compounds of formulae (amines K and L)

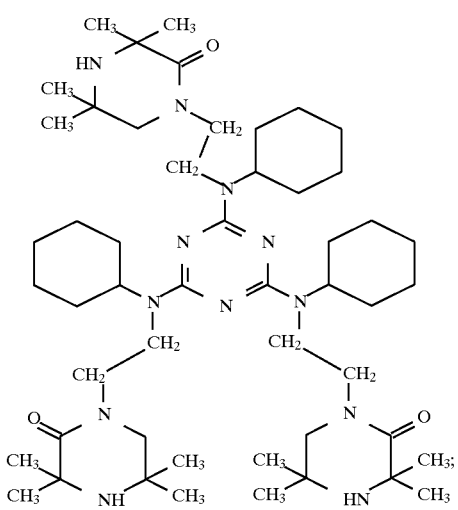

and

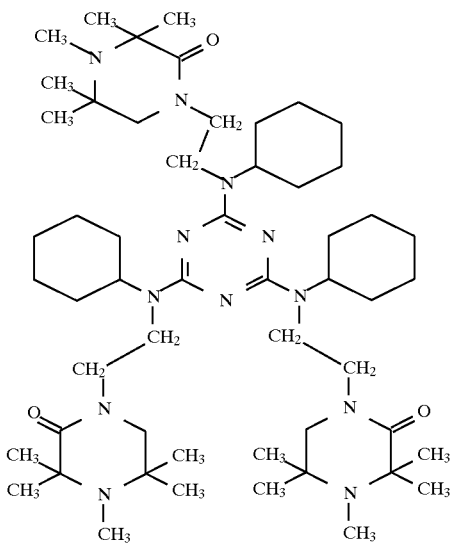

compounds of formula X, wherein n is 2, $G^{11}$ is hydrogen or methyl, and $G^{14}$ is $C_2$–$C_{12}$alkylene; a particularly interesting amine of this class is the compound (100) [=amine M] described above, as well as the oligomeric compounds having 2 to 10 structural repeating units obtainable by reaction (i) of

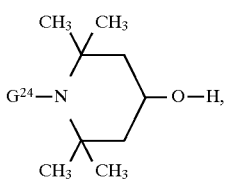

wherein $G^{24}$ is $C_2$–$C_5$hydroxyalkyl, with an aliphatic $C_2$–$C_{12}$dicarboxylic acid or a suitable reactive derivative such as the diester, the dichloride or the anhydride;

(j) of a linear oligomeric polyester of a diol and butane-1,2,3,4-tetracarboxylic acid with 2,2,6,6-tetramethyl-4-hydroxy-piperidine;

(k) of

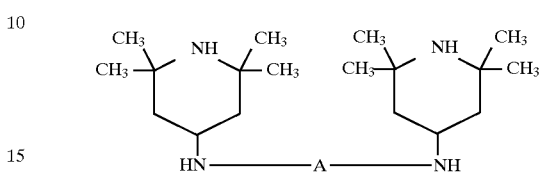

with

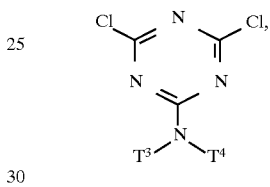

wherein A is $C_2$–$C_6$alkylene, $T^3$ is $C_1$–$C_{18}$alkyl or cyclohexyl, $T^4$ is hydrogen or $C_1$–$C_{18}$alkyl, or $T^3$ and $T^4$, taken together, are $C_4$–$C_6$alkylene or $C_3$–$C_5$oxaalkylene;

(l) of $H_2N$—A—NH—A—$NH_2$ with

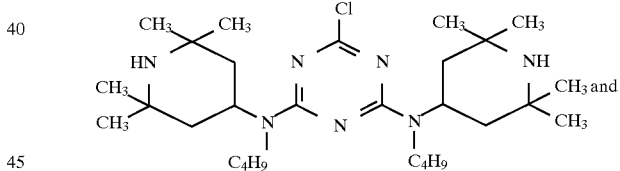

Br—A—Br, wherein A is $C_2$–$C_6$alkylene;

(m) of compounds of formula

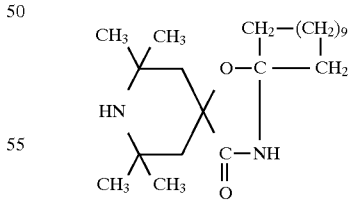

with epichlorohydrin;

(n) of

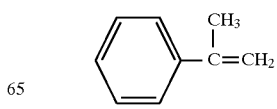

with
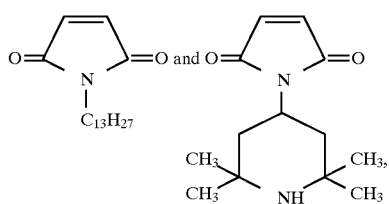
as well as oligomeric compounds of formula (o)
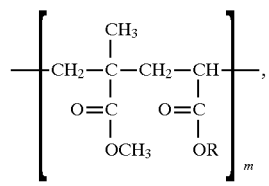
wherein about one third of the radicals R are —$C_2H_5$ and the others are
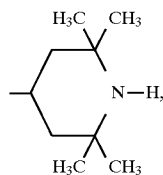
and m is a number from 2 to 10;
particularly interesting oligomeric amines are those of formulae (m again is a number from 2 to 10)
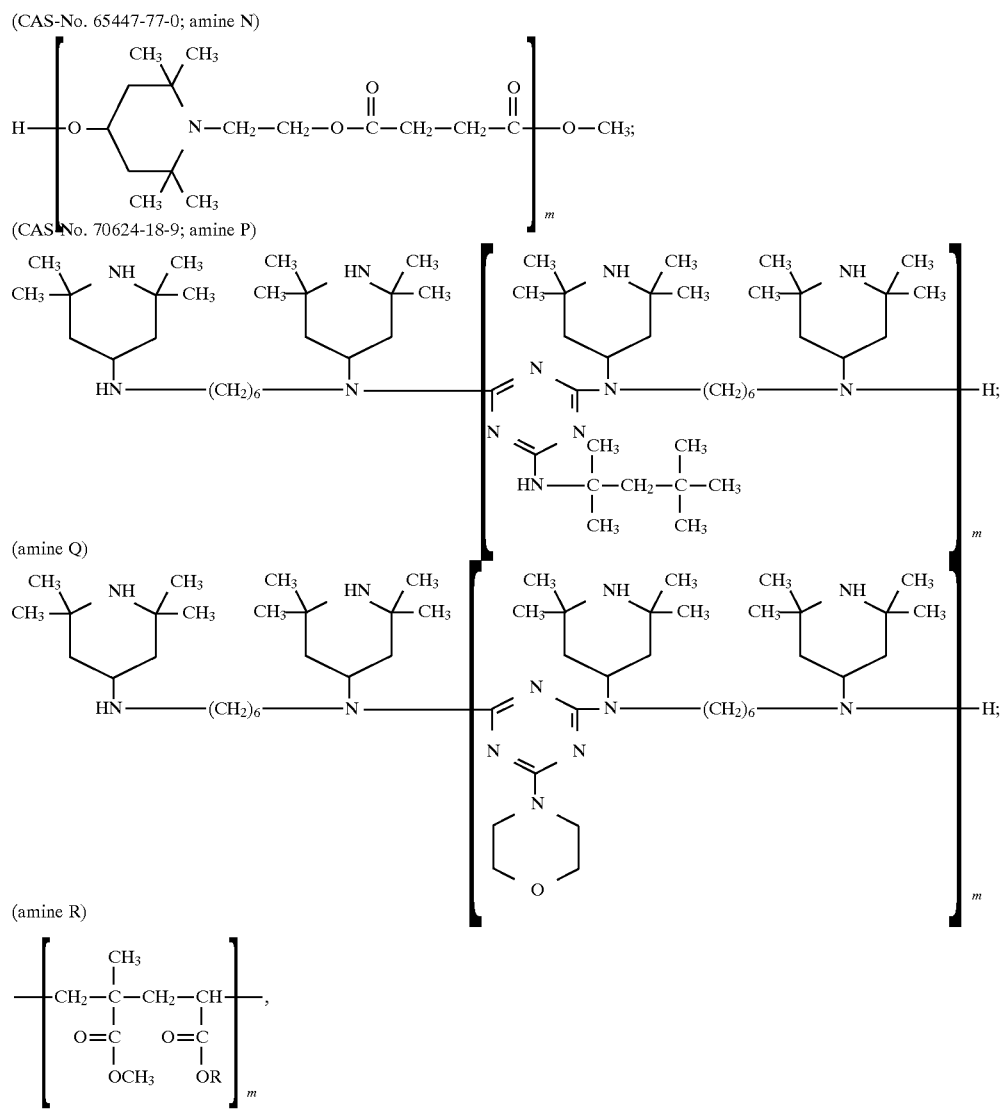

wherein about one third of the radicals R are —C₂H₅ and the other are

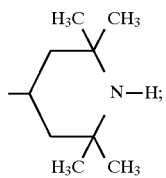

a linear polyester having 2 to 10 structural repeating units of butane-1,2,3,4-tetracarboxylic acid and a diol of formula

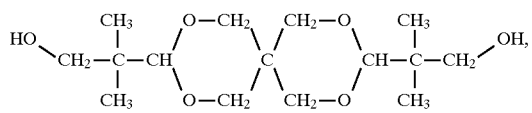

wherein the end groups and the side-chains are formed by esterification of the free carboxyl groups with 2,2,6,6-tetramethyl-4-hydroxy-piperidine (amine S); a copolymer, whose structural repeating unit is composed of 2 units

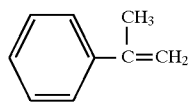

and 1 unit each of

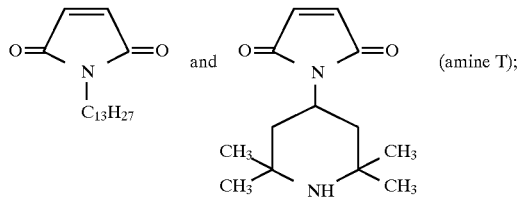

the reaction product of H₂N—(CH₂)₂—NH—(CH₂)₂—NH₂ with

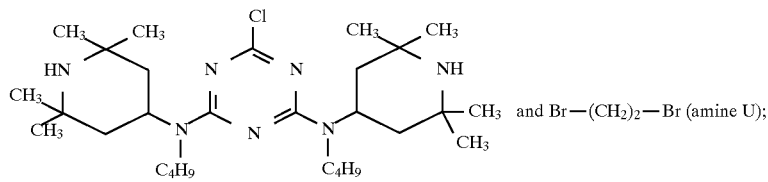

and the reaction product of the compound of formula

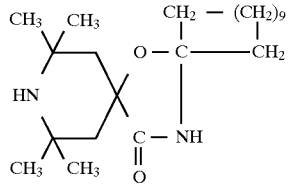

with epichlorohydrine (amine W).

The oligomeric amines are often a mixture of compounds which differ from each other with respect to the length of their chains.

Of preeminent interest is the use of the amines A, B, C, D, E, F, G, H, J, K, L, M, N, O, P, Q, R, S, T, U, V and W specified above.

It is particularly preferred to add to the novel compositions those amines whose molecular weight or average molecular weight $\overline{M}_n$ is in the range from 300 to 10000, more particularly from 1000 to 10000. To be highlighted in particular are in turn those amines whose molecular weight or average molecular weight is $\overline{M}_n$ is in the range from 1500 to 10000, e.g. from 2000 to 7500. The amines of higher molecular weight are, in particular, sterically hindered amines.

To be highlighted in particular are those novel compositions comprising as component (b) two or more than two compounds of the type of the sterically hindered amines.

The indicated amines are known compounds; many of them are commercially available.

The novel compositions preferably comprise phosphites or phosphonites corresponding to one of formulae (1) to (7)

  (1)

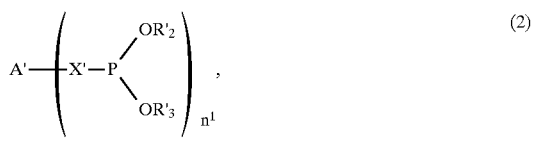  (2)

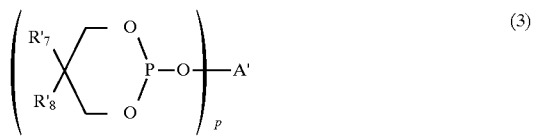  (3)

-continued

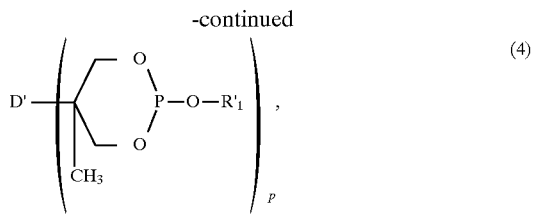  (4)

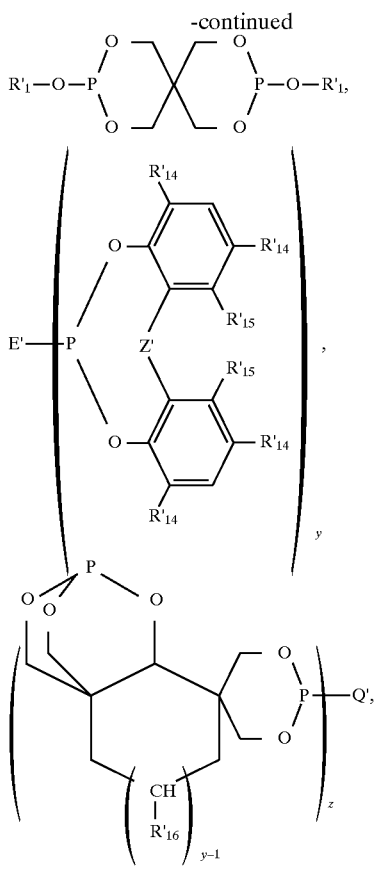

(5)

(6)

(7)

wherein the indices are integers, and n' is 2, 3 or 4; p is 1 or 2; q is 2 or 3; r is 4 to 12; y is 1, 2 or 3; and z is 1 to 6;

A', if n'=2, is alkylene of 2 to 18 carbon atoms; alkylene of 2 to 12 carbon atoms which is interrupted by —S—, —O— or —NR'$_4$—; a radical of one of formula

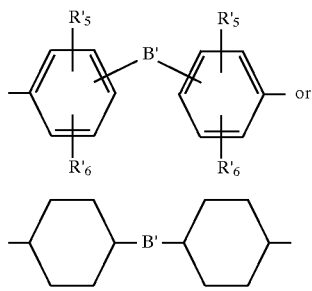

or phenylene;

A', if n'=3, is a radical of formula —C$_r$H$_{2r-1}$—;

A', if n'=4, is the radical of formula C(CH$_2$—)$_4$;

A", if n'=2, has the meaning of A';

B' is a radical of formula —CH$_2$—; —CHR'$_4$—; —CR'$_1$R'$_4$—; —S— or a direct bond; or C$_5$–C$_7$cycloalkylidene; or cyclohexylidene which is substituted by 1 to 4 C$_1$–C$_4$alkyl radicals in position 3, 4 and/or 5;

D', if p=1, is methyl and, if p=2, is —CH$_2$OCH$_2$—;

E', if y=1, is alkyl of 1 to 18 carbon atoms, a radical of formula —OR'$_1$ or halogen;

E', if y=2, is a radical of formula —O—A"—O—;

E', if y=3, is a radical of formula R'$_4$C(CH$_2$O—)$_3$;

Q' is the radical of an at least z-hydric alcohol or phenol, which radical is bound through the alcoholic or phenolic O-atom(s) to the P-atom(s);

R'$_1$, R'$_2$ and R'$_3$ are each independently of one another alkyl of 1 to 30 carbon atoms; alkyl of 1 to 18 carbon atoms which is substituted by halogen, —COOR$_4$', —CN or —CONR$_4$'R$_4$';

alkyl of 2 to 18 carbon atoms which is interrupted by —S—, —O— or —NR'$_4$—;

phenyl-C$_1$–C$_4$alkyl; cycloalkyl of 5 to 12 carbon atoms; phenyl or naphthyl; phenyl or naphthyl which is substituted by halogen, 1 to 3 alkyl radicals or alkoxy radicals of a total of 1 to 18 carbon atoms, or by phenyl-C$_1$–C$_4$alkyl; or a radical of formula

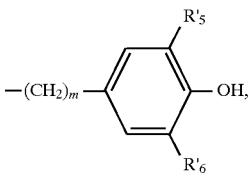

wherein m is an integer from 3 to 6;

each R'$_4$ is independently hydrogen; alkyl of 1 to 18 carbon atoms; cycloalkyl of 5 to 12 cabon atoms; or phenylalkyl of 1 to 4 carbon atoms in the alkyl moiety;

R'$_5$ and R'$_6$ are each independently of the other hydrogen; alkyl of 1 to 8 carbon atoms or cycloalkyl of 5 or 6 carbon atoms; R'$_7$ and R'$_8$, if q=2, are each independently of the other C$_1$–C$_4$alkyl or, taken together, are a 2,3-dehydropentamethylene radical; and R'$_7$ and R'$_8$, if q=3, are methyl; the substituents R'$_{14}$ are each independently of one another hydrogen; alkyl of 1 to 9 carbon atoms or cyclohexyl;

the substituents R'$_{15}$ are each independently of one another hydrogen or methyl; and R'$_{16}$ is hydrogen or C$_1$–C$_4$alkyl and, if there is more than one radical R'16, said radicals R'$_{16}$ are identical or different;

X' and Y' are each a direct bond or —O—; and

Z' is a direct bond; —CH$_2$—; —C(R'$_{16}$)$_2$— or —S—.

A particularly preferred process is that wherein the phosphite or phosphonite is one of formula (1), (2), (5) or (6), wherein n' is 2, and y is 1 or 2;

A' is alkylene of 2 to 18 carbon atoms; p-phenylene or p-biphenylene;

E', if y=1, is C$_1$–C$_{18}$alkyl, —OR$_1$ or fluoro; and, if y=2, is p-biphenylene;

R'$_1$, R'$_2$ and R'$_3$ are each independently of one another alkyl of 1 to 18 carbon atoms; phenyl-C$_1$–C$_4$alkyl; cyclohexyl; phenyl; phenyl which is substituted by 1 to 3 alkyl radicals containing a total of 1 to 18 carbon atoms;

the substituents R'$_{14}$ are each independently of one another hydrogen or alkyl of 1 to 9 carbon atoms;

R'$_{15}$ is hydrogen or methyl;

X' is a direct bond;

Y' is —O—; and

Z' is a direct bond or —CH(R'$_{16}$)—.

A process meriting particular interest is a process for stabilising a phosphite or phosphonite of one of formula (1), (2), (5) or (6), wherein n' is 2, and y is 1;

A' is p-biphenylene;

E' is $C_1$–$C_{18}$alkoxy or fluoro;

$R'_1$ $R'_2$ and $R'_3$ are each independently of one another alkyl of 1 to 18 carbon atoms;

phenyl substituted by 2 or 3 alkyl radicals containing a total of 2 to 12 carbon atoms; the substituents $R'_{14}$ are each independently of one another methyl or tert-butyl;

$R'_{15}$ is hydrogen;

X' is a direct bond;

Y' is —O—; and

Z' is a direct bond, —$CH_2$— or —$CH(CH_3)$—.

Phosphites are particularly preferred, especially those of formulae (1) and (5).

The following compounds are exemplary of phosphites and phosphonites whose stability to hydrolysis can be particularly advantageously enhanced by the novel process:

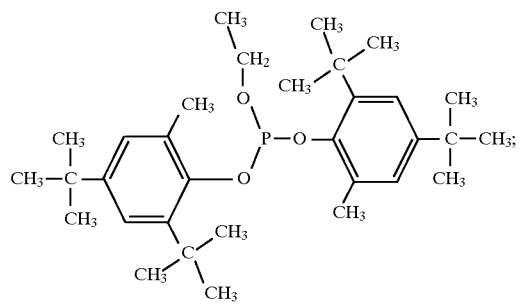
(Ph-1)

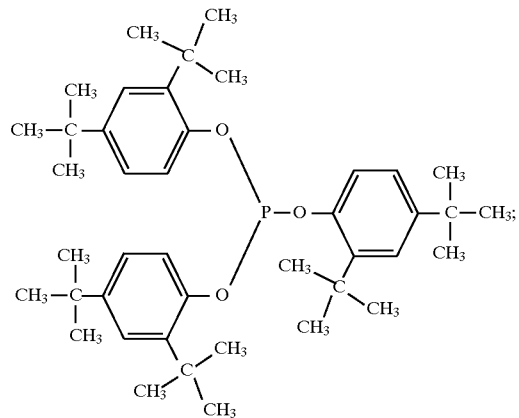
(Ph-2)

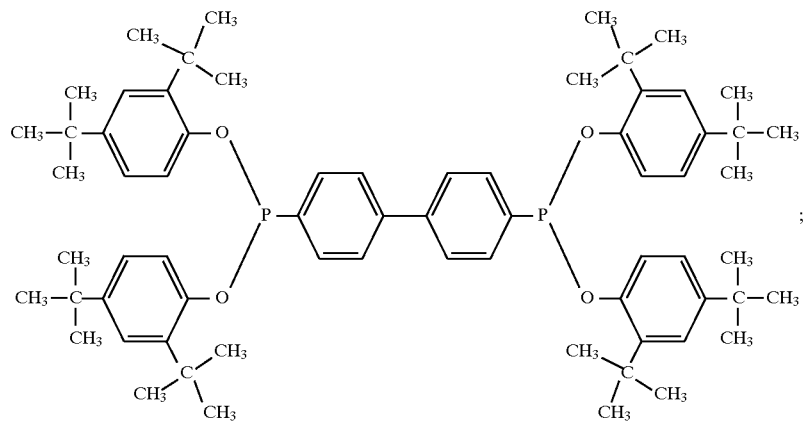
(Ph-3)

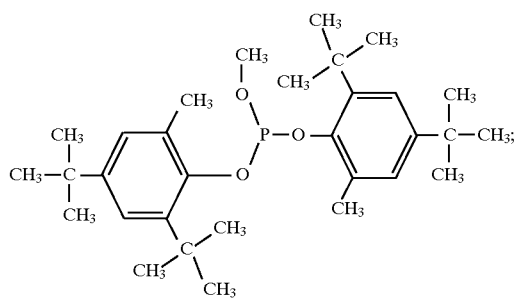
(Ph-4)
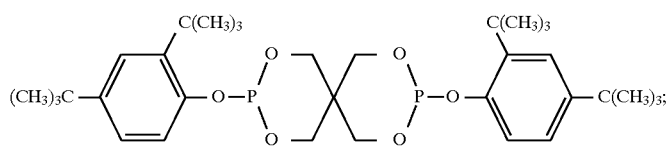
(Ph-5)
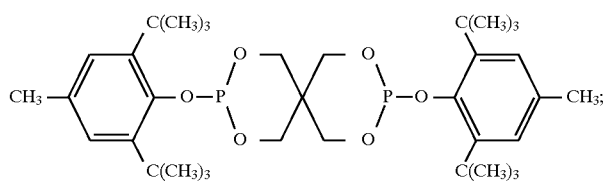
(Ph-6)
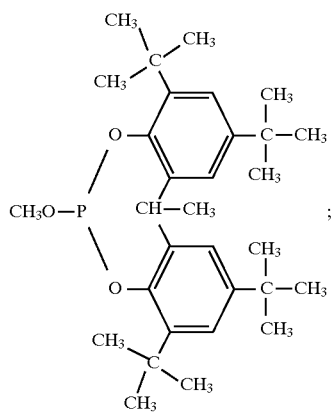
(Ph-7)
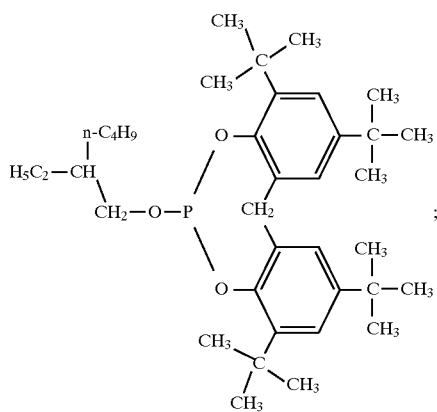
(Ph-8)

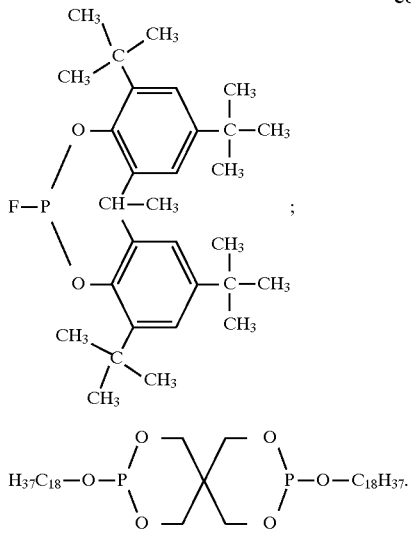

(Ph-9)

(Ph-10)

Said phosphites and phosphonites are known compounds; some of them are commercially available.

The invention also relates to a process for stabilising an organic phosphite or phosphonite or a mixture of organic phosphites or phosphonites against hydrolysis, which comprises adding as stabiliser (b) an organic amine and as stabiliser (c) an acid-binding metal salt, such that the stabilised phosphite or phosphonite comprises 0.001 to 50% by weight, especially 0.01 to 50% by weight, of the aminic component (b) and 0.01 to 25% by weight of the acid-binding metal salt (c) (in each case based on the total weight), as well as to the use of an organic amine in conjunction with an acid-binding metal salt as hydrolysis stabiliser for organic phosphites or phosphonites. Preferred amounts and single components for use in the novel process are as indicated above.

The invention also relates to an organic phosphite or phosphonite stabilised against hydrolysis obtainable by the above-described process.

It is preferred to use sterically hindered amines in combination with acid-binding metal salts, more particularly sterically hindered amines having a molecular weight, or an average molecular weight, in the range from 1500 to 10000 and, most preferably, in conjunction with hydrotalcites and/or zeolites, as stabilisers for organic phosphites and/or phosphonites against hydrolysis, particularly against hydrolysis during storage in contact with humid air. The use as hydrolysis stabilisers for organic phosphites is particularly preferred. To achieve the desired enhanced hydrolysis stability, any amount of a sterically hindered amine and acid-binding metal salt can be used, for example 0.01 to 200% by weight, more particularly 0.1 to 100% by weight, preferably 0.01 to 50% by weight and, most preferably, 0.1 to 25% by weight, in each case based on the amount of phosphite or phosphonite. The amount of acid-binding metal salt is expediently at least 0.01% by weight, based on the stabilised composition.

At the same time, the invention relates to a method of storing solid organic phosphites or phosphonites, which comprises adding to said phosphites or phosphonites 0.001 to 200% by weight, typically 0.01 to 100% by weight, preferably 0.01 to 50% by weight and, most preferably, 0.1 to 25% by weight (based on phosphite or phosphonite) each of a sterically hindered amine and an acid-binding metal salt.

Some commercial organic phosphites or phosphonites are obtained as compound mixtures or in prestabilised form; an organic amine is often used as prestabiliser in a concentration of c. 1%. The stability to hydrolysis of such products can also be greatly enhanced by the novel process.

The novel compositions and the products obtained by the novel process may advantageously be used as stabilisers for organic material, in particular organic polymers, typically synthetic polymers, against the harmful action of heat, oxygen and/or light. Illustrative examples of such polymers are disclosed, inter alia, in U.S. Pat. No. 4,855,345, from column 4, line 63, to column 7, line 54.

Amine and acid-binding metal salt (components b and c) can be added to the phosphite or phosphonite by customary mixing procedures or, for example, by milling them together. They are conveniently added to the solution or melt of the phosphite or phosphonite prior to the crystallisation thereof, e.g. to the solution resulting from the synthesis. It is also possible to add said components during the synthesis or to one of the educts.

In the novel process it is possible to use crude phosphite solutions or crude phosphonite solutions as obtained from the synthesis before crystallisation.

In a preferred embodiment, the organic amine and the acid-binding metal salt are added to a solution or a melt from which the phosphite or phosphonite is crystallised. In this case the amount of amine added to the solution or melt is usually 0.01 to 100% by weight, preferably 0.01 to 50% by weight, more particularly 0.1 to 25% by weight and, most preferably, 0.5 to 20% by weight (in each case based on the phosphite or phosphonite). The amount of acid-binding metal salt in the solution or melt is expediently 0.05 to 25% by weight, based on the total weight of the solution or melt, without taking into account any solvent present, as indicated at the outset with respect to the product. The use of 0.05 to 25% by weight of acid-binding metal salt, based on the phosphite or phosphonite, is preferred.

The crystalline phosphite or phosphonite can then be obtained from the solution or melt in per se known manner, typically by cooling and/or concentration. It is possible to accelerate the crystallisation by addition of seed crystals. The solution can conveniently be concentrated by heating, by applying reduced pressure, by using entrainers and/or by cold trapping. If required, further customary working up processes can then follow, such as filtration, drying or milling. In a preferred process, the acid binding metal salt is added to the solution or melt of the phosphite or phosphonite, which is subsequently subjected to a coarse filtration, then the organic amine is added, followed by crystallization of the product.

The product of the novel process is a mixture comprising solid phosphite or phosphonite, acid-binding metal salt and amine. The product of the novel process preferably contains mixed crystals of amine and phosphite or phosphonite in admixture with crystals of the acid-binding metal salt. These mixed crystals preferably constitute at least 50% by weight, more particularly at least 80% by weight, of the product.

A particularly preferred process for stabilising a crystalline organic phosphite or phosphonite against hydrolysis comprises adding a homogeneous melt, heated to 50°–100° C., of phosphite or phosphonite, of a solvent or solvent mixture, and of 0.1 to 100% by weight (based on phosphite or phosphonite) of an amine, in which melt 0.05 to 25% of acid-binding metal salt (based on phosphite or phosphonite) are dispersed, to a liquid crystallisation medium, the temperature of which during the addition is kept at 10°–70° C. below the temperature of the melt.

The melt in this process is the liquid mixture comprising amine, solvent and the phosphite or phosphonite to be stabilised. The melt may contain a minor or larger amount of solvent, e.g. 20 or 500% by weight (based on phosphite or phosphonite), and accordingly the melt can have the character of a solution. It is important that the melt is homogeneous, i.e. that the indicated components are no longer crystalline and also that there is no separation into two or more than two liquid phases. The amine can be a single compound or a mixture of compounds.

The acid-binding metal salt is conveniently added to the mixture before or during the homogenisation in finely particulate form and dispersed in known manner, typically by stirring.

As solvent there may be used in principle all organic compounds or compound mixtures which are liquid in the temperature range from 10° to 60° C. under normal pressure and do not cause solvolysis, and which are capable of dissolving a sufficient amount of solid phosphite or phosphonite above 50° C. and, as appropriate, at up to 100° C., or which are sufficiently miscible with the fused phosphite or phosphonite. The solubility or miscibility is sufficient when, for example, the homogeneous liquid mixture is able to contain up to and including 15% by weight, more particularly up to and including 50% by weight, of phosphite or phosphonite. Suitable solvents are e.g. alcohols or hydrocarbons, or mixtures thereof.

The solvent used in the melt is preferably a compound or a mixture of two compounds. The main solvent is used in an amount of 20 to 500% by weight, based on phosphite or phosphonite, and the further solvent is used in amount of 0–50% by weight, based on the main solvent. The melt preferably contains as main solvent an alcohol or a hydrocarbon in an amount of 20 to 500% by weight, based on phosphite or phosphonite, and a further solvent in an amount of 0–50% by weight, more particularly of 0–20%, based on the main solvent.

It is also possible to use a mixture of alcohols or a mixture of hydrocarbons.

Suitable alcohols are, for example, lower alcohols such as $C_1$–$C_5$alkanols, more particularly $C_1$–$C_3$alkanols such as methanol, ethanol, propanol or isopropanol. Isopropanol and methanol are particularly suitable. Suitable hydrocarbons are typically $C_6$–$C_{13}$alkanes, cycloalkanes or alkylated cycloalkanes of 6 to 12 carbon atoms, benzene, or alkylated aromatic hydrocarbons of 6 to 10 carbon atoms. Toluene, ligroin, petroleum ether and xylene are particularly suitable. Toluene is most preferred.

A hydrocarbon or a mixture of hydrocarbons is often used as further solvent if the main solvent is an alcohol or, if the main solvent is a hydrocarbon, an alcohol. Suitable alcohols and hydrocarbons are those indicated above.

The temperature of the melt is preferably in the range from 55° to 90° C., more particularly from 60° to 80° C.

In the preferred process the difference in temperature between the melt and the crystallisation medium is conveniently at least 20° C., typically from 30° to 70° C. and, preferably, from 40° to 60° C.

The crystallisation medium is preferably kept at a temperature which is at least 10° C., typically from 10° to 60° C., below the resulting liquidus temperature. The temperature of the crystallisation medium is preferably from 20° to 60° C. below the resulting liquidus temperature.

The resulting liquidus temperature is the temperature at which a homogeneous phase formed from melt and crystallisation medium is in thermodynamic equilibrium with phosphite crystals or phosphonite crystals. Below this temperature, crystallisation begins; above this temperature, the mixture is a homogeneous melt. In practice, said temperature is conveniently determined by mixing experiments, typically using calorimetric methods (e.g. DSC) and/or optical methods.

As crystallisation medium it is expedient to use 80 to 800% by weight, more particularly 100 to 500% by weight, of organic solvent, based on phosphite or phosphonite in the melt.

Alcohols can conveniently be used as crystallisation medium, for example a $C_1$–$C_5$alkanol or a mixture of different $C_1$–$C_5$alkanoles. It is preferred to use $C_1$–$C_3$alkanols as crystallisation medium, e.g. methanol, ethanol, propanol or isopropanol.

It is expedient to add seed crystals to the crystallisation medium. Accordingly, the crystallisation medium preferably consists of a suspension of 2 to 20% by weight of crystalline phosphite or phosphonite, based on phosphite or phosphonite in the melt. Furthermore, it is advantageous if the crystallisation medium is saturated 50 to 100% with the amine, 100% saturation corresponding to an amine concentration in which dissolved and solid amines may be obtained simultaneously.

The melt usually comprises 0.1 to 50% by weight of amine (component b), based on phosphite or phosphonite, preferably 0.2 to 25% by weight, more particularly 0.5 to 20% and, most preferably 0.5 to 10% (based on phosphite or phosphonite in the melt).

The acid-binding metal salt (component c) is usually added to the melt in an amount of 0.05 to 20% by weight, more particularly of 0.05 to 15% by weight and, most preferably, of 0.1 to 10% by weight (based on phosphite or phosphonite in the melt).

The crystallisation medium is preferably stirred when adding the melt and component (c) dispersed therein. After the two mixtures have been combined, the further working up can be carried out in per se known manner, e.g. by cooling to 10°–15° C. and by isolation of the crystalline product.

The stabilised phosphite or phosphonite is usually obtained in powdered form, wherein the amine and the acid-binding metal salt are homogeneously dispersed. The powder typically comprises 0.001 to 20% by weight, e.g. 0.01 to 20% by weight, more particularly 0.05 to 10% by weight and, preferably, 0.1 to 5% by weight of amine (based on phosphite or phosphonite). After crystallisation, the metal salt dispersed in the melt is often present in almost quantitative amount in the product. If the melt is additionally filtered, which may be expedient on account of the apparatus employed, the content of acid-binding metal salt also can be reduced, often minimally.

The preferred process is particularly useful for stabilising the above-mentioned phosphites Ph-1, Ph-2, Ph-4, Ph-5, Ph-6, Ph-7 and Ph-8, and the phosphonite Ph-3.

The following Examples further illustrate the novel process. Unless otherwise stated, all parts and percentages are by weight, as likewise in the remainder of the description and in the claims. Percentages relating to phosphite or phosphonite will be taken to mean phosphite or phosphonite in the melt, unless otherwise stated.

Amines used in the Examples are:

amine A: triisopropanolamine;

amine C: bis(2,2,6,6-tetramethylpiperidin-4-yl)sebacate amine H: compound of formula

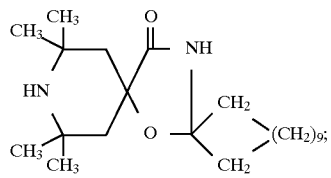

amine J: compound of formula

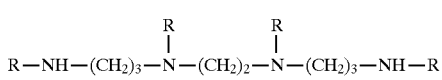

wherein R

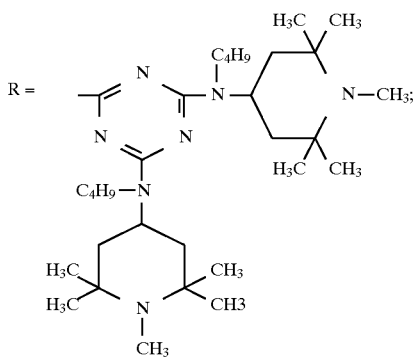

CAS-No. 106990-43-6;

amine N: oligomer of formula

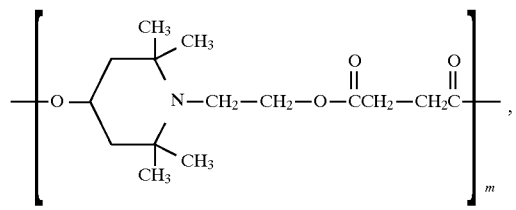

wherein m is a number from 8 to 11; CAS-No. 65447-77-0;

amine P: oligomer of formula

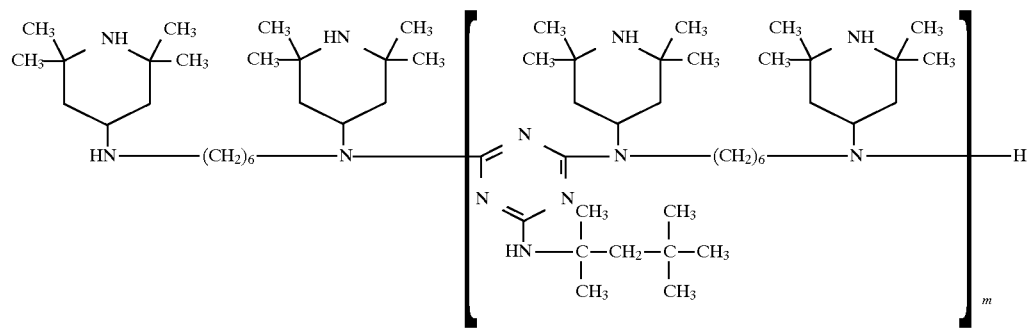

wherein m is a number from 3 to 4 (CAS-No. 70624-18-9);

amine Q: oligomer of formula

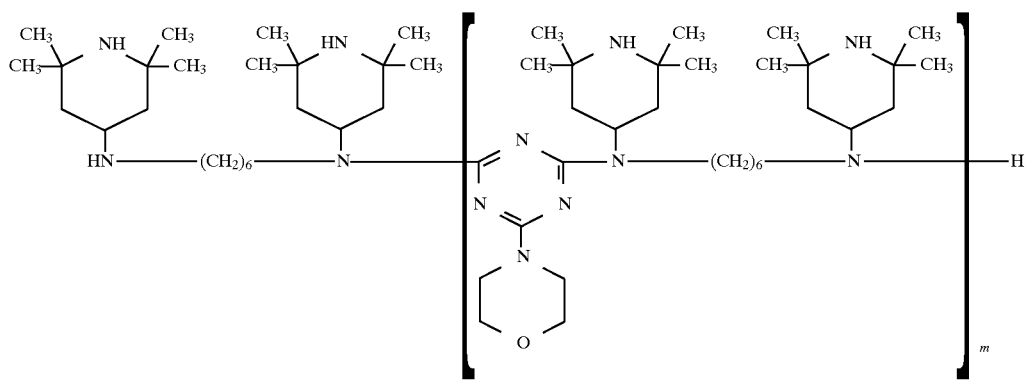

(supplied by Cytec Inc., USA);

amine U: reaction product of $H_2N-(CH_2)_2-NH-(CH_2)_2-NH_2$ with

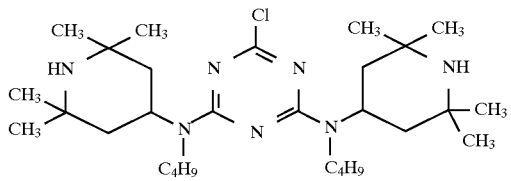

and $Br-(CH_2)_2-Br$ (supplied by: Sigma);

amine X: 2,2,6,6-tetramethylpiperidine;

amine Y: 4-hydroxy-2,2,6,6-tetramethylpiperidine (HTMP);

amine Z: 1,3,5-trimethyl-2,4,6-triazine.

The zirconium carbonate (Zr carb.) used in some of the Examples as acid-binding metal salt is basic zirconium carbonate, supplied by Tilcom, Great Britain.

If not indicated in the Example or in the above list, the structural formulae of the phosphites, phosphonites and amines used in the Examples are listed in the text above.

EXAMPLE 1

A mixture of 300 g of the phosphite Ph-1, 225 g of isopropanol, 2.25 g of toluene, 6.0 g of the metal salt of formula IXc $$Mg_{4.5}Al_2(OH)_{13}.CO_3.3.5H_2O, \text{ (IXc)}$$

(stabiliser IXc; Kyowa Chem. Ind., Osaka, Japan) and 30 g of amine N is heated, with stirring, to 70°–75° C. The resulting homogeneous melt containing dispersed metal salt is subjected to coarse filtration and then added over 1 hour, with stirring, to 450 g of isopropanol, the temperature of which is kept at 20°–30° C. during this addition. The mixture is then cooled to 10°–15° C. and stirred for another 3 hours in this temperature range. The crystalline product is then isolated by filtration and dried at 60° C. under reduced pressure (sample d). The elemental analysis of the dried product gives a content of 9.0% of amine N and 0.19% of metal salt (based on phosphite).

Three comparison samples are crystallised by the method described above, but using in one sample the amine (sample c), in the second sample the metal salt (sample b), and in the third sample both additions are omitted (sample a).

Another sample (e) is crystallised by the above method, but further adding 6.0 g of amine P to the melt. The elemental analysis of the dry product gives a content of 9% of amine N, 0.5% of amine P and 0.19% of metal salt (based on phosphite).

Equal amounts of the product are then subjected to the following test for stability to hydrolysis:

The samples are stored at 50° C. and 75% atmospheric humidity. The content of phosphite Ph-1 is determined at regular intervals by means of gas chromatography (begin of storage is set as 100% Ph-1).

The results are shown in the following Table 1.

TABLE 1

Degradation of the phosphite Ph-1 during storage at 50° C. and 75% humidity

| Sample | Stabiliser | Stab. in product | Degradation (%) after | | |
|---|---|---|---|---|---|
| | | | 0 h | 24 h | 41 h |
| a | none | none | 0 | 100 | 100 |
| b | 10% amine N | 9.0% amine N | 0 | 13.6 | 35.9 |
| c | 2% IXc | 1.7% IXc | 0 | 11.5 | 77.8 |
| d | 10% amine N + 2% IXc | 9.0% amine N + 0.19% IXc | 0 | 5.2 | 17.0 |
| e | 10% amine N + 2% IXc + 2% amine P | 9.0% amine N + 0.19% IXc + 0.5% amine P | 0 | 6.5 | 15.0 |

The results in Table 1 show that the phosphite samples d and e of this invention have excellent stability to hydrolysis.

EXAMPLE 2

Stabilised phosphite Ph-1 is prepared according to the method described in Example 1 and tested for stability to hydrolysis; the content of undegraded phosphite is determined by $^{31}$P-NMR after a storage time of 24 h, 48 h and 72 h. The following Table 2 shows the amount and type of amine and metal salt used as well as the test results.

TABLE 2

Degradation of the phosphite Ph-1 during storage at 50° C. and 75% humidity; amount based on phosphite

| Metal salt in of Ph-1 | in product | Amine of Ph-1 | in product | Phosphite content (%) after | | |
|---|---|---|---|---|---|---|
| | | | | 24 h | 48 h | 72 h |
| 0 (unstabilised) | 0 | 0 | 0 | 48.3 | 0 | 0 |
| 0 | 0 | 10% amine N | 8% | 79.4 | 21.2 | 0 |
| 0 | 0 | 10% amine P | 1.4% | 88.5 | 22.2 | 0 |
| 0 | 0 | 10% amine A | 0.35% | 60.4 | 15.6 | 0 |
| 0 | 0 | 10% piperazine | 0.35% | 62.1 | 20.2 | 0 |

TABLE 2-continued

Degradation of the phosphite Ph-1 during storage at 50° C. and 75% humidity; amount based on phosphite

| Metal salt of Ph-1 | in product | Amine of Ph-1 | in product | Phosphite content (%) after 24 h | 48 h | 72 h |
|---|---|---|---|---|---|---|
| 2% IXc | 1.1% | 0 | 0 | 85.7 | 20.3 | 0 |
| 10% IXc | 1.3% | 10% piperazine | 0.02% | 90.1 | 81.3 | 60.2 |
| 10% IXc | 1.2% | 10% amine X | 0.03% | 85.8 | 75.2 | 51 |
| 10% IXc | 1.4% | 10% amine Z | 0.04% | 87 | 78.1 | 52.4 |
| 10% IXc | 1.6% | 10% dibutylamine | 0.01% | 90.2 | 81.5 | 60.5 |
| 10% IXc | 1.4% | 10% amine J | 0.2% | 100 | 95.8 | 80.4 |
| 10% IXc | 1.5% | 10% amine C | 0.18% | 94.5 | 89.8 | 72 |
| 10% IXc | 1.3% | 10% amine H | 0.19% | 98.4 | 92.1 | 75.9 |
| 10% IXc | 1.2% | 10 amine U | 0.15% | 96.3 | 90.8 | 74.1 |
| 10% IXc | 1.4% | 10 amine Q | 0.21% | 100 | 94.2 | 78.3 |
| 0.5% IXc | 0.06% | 0.5% piperazine | 0.015% | 85.3 | 74.1 | 50.9 |
| 0.5% IXc | 0.07% | 0.5% amine X | 0.02% | 79.7 | 68.9 | 45.2 |
| 0.5% IXc | 0.08% | 0.5% amine Z | 0.01% | 81.2 | 72.6 | 46.1 |
| 0.5% IXc | 0.06% | 0.5% dibutylamine | 0.01% | 84 | 75.9 | 54.2 |
| 0.5% IXc | 0.07% | 0.5% amine J | 0.02% | 98.4 | 90.8 | 75.2 |
| 0.5% IXc | 0.07% | 0.5% amine C | 0.03% | 90 | 84.2 | 66 |
| 0.5% IXc | 0.08% | 0.5% amine H | 0.02% | 93.3 | 87.4 | 71 |
| 0.5% IXc | 0.09% | 0.5% amine U | 0.02% | 91.5 | 85.7 | 69.1 |
| 0.5% IXc | 0.06% | 0.5% amine Q | 0.02% | 97.3 | 88.4 | 71.4 |
| 2% IXc | 1.1% | 10% amine N | 8% | 91.7 | 77.8 | 63.8 |
| 0.5% IXc | 0.2% | 0.5% amine N | 0.3% | 88.3 | 70.1 | 53.2 |
| 10% ZnO | 1.4% | 10% amine A | 0.22% | 85.4 | 73.2 | 48.5 |
| 10% ZnO | 1.3% | 10% amine N | 8.3% | 89.8 | 75 | 59.4 |
| 10% ZnO | 1.5% | 10% amine P | 0.24% | 98.6 | 90.4 | 72.2 |
| 0.5% ZnO | 0.06% | 0.5% amine A | 0.05% | 80.1 | 61.8 | 35.4 |
| 0.5% ZnO | 0.08% | 0.5% amine N | 0.21% | 84.6 | 66.4 | 49.9 |
| 0.5% ZnO | 0.07% | 0.5% amine P | 0.04% | 95.8 | 86.3 | 69.1 |
| 10% CaO | 1.3% | 10% piperazine | 0.03% | 85 | 75.4 | 53.2 |
| 10% CaO | 1.4% | 10% amine P | 0.27% | 97.2 | 89.8 | 71.4 |
| 10% CaO | 1.2% | 10% amine J | 0.26% | 95.4 | 86.9 | 68.1 |
| 10% CaO | 1.2% | 10% amine U | 0.27% | 91.8 | 82.4 | 61.9 |
| 0.5% CaO | 0.1% | 0.5% piperazine | 0.02% | 78 | 68.8 | 42 |
| 0.5% CaO | 0.08% | 0.5% amine P | 0.03% | 90.6 | 83.4 | 65.9 |
| 0.5% CaO | 0.07% | 0.5% amine J | 0.02% | 87.9 | 79.1 | 60 |
| 0.5% CaO | 0.09% | 0.5% amine U | 0.03% | 84.1 | 75.9 | 53 |
| 10% MgO | 1.3% | 10% amine J | 0.25% | 94.8 | 88.1 | 70 |
| 10% MgO | 1.2% | 10% amine C | 0.23% | 88.2 | 79.2 | 60.2 |
| 0.5% MgO | 0.08% | 0.5% amine J | 0.02% | 86.8 | 78 | 58 |
| 10% CaCO$_3$ | 1.3% | 10% amine P | 0.25% | 90.8 | 83 | 50.4 |
| 10% CaCO$_3$ | 1.4% | 10% amine H | 0.26% | 89.4 | 81.1 | 43.7 |
| 0.5% CaCO$_3$ | 0.08% | 0.5% amine P | 0.02% | 85.4 | 78.4 | 42.9 |
| 10% Ca(OH)$_2$ | 1.6% | 10% amine Q | 0.27% | 90.4 | 82.6 | 48.7 |
| 2% Zr carb. | 1.2% | 10% amine N | 6.3% | 85.6 | 66 | 43.8 |
| 0.5% Zr carb. | 0.15% | 0.5% amine N | 0.23% | 80.4 | 57.3 | 32.5 |
| 2% Al(OH)$_3$ | 1.1% | 10% amine N | 6.3% | 76.3 | 50.6 | 42.3 |
| 0.5% Al(OH)$_3$ | 0.2% | 0.5% amine N | 0.25% | 73.2 | 41.8 | 25.6 |

EXAMPLE 3

Stabilised phosphite Ph-2 is prepared according to the method described in Example 1. Stability to hydrolysis is determined by storing at 70° C. and 75% atmospheric humidity, and the content of undegraded phosphite is tested by $^{31}$P-NMR after a storage time of 24 h, 48 h and 72 h. The following Table 3 shows the amount and type of the amine and metal salt used as well as the test results.

TABLE 3

Degradation of the phosphite Ph-2 during storage at 70° C. and 75% humidity; amount based on phosphite

| Metal salt of Ph-2 | in product | Amine of Ph-2 | in product | Phosphite content (%) after 24 h | 48 h | 72 h |
|---|---|---|---|---|---|---|
| 0 (unstabilised) | | 0 | 0 | 95.4 | 60.3 | 0 |
| 0 | 0 | 10% amine J | 1.6% | 97.1 | 86 | 21.4 |
| 0 | 0 | 10% amine N | 8.7% | 97.2 | 85.3 | 20.6 |
| 0 | 0 | 10% amine A | 1.55 | 80.2 | 25.4 | 0 |
| 10% IXc | 3.8% | 0 | 0 | 90.2 | 40.9 | 0 |
| 10% IXc | 3.6% | 10% amine J | 1.5% | 100 | 96 | 74.1 |
| 10% IXc | 3.7% | 10% amine N | 8.7% | 100 | 95.3 | 70.2 |
| 10% IXc | 3.6% | 10% amine A | 0.9% | 100 | 80.6 | 45.3 |
| 0.5% IXc | 0.26% | 0.5% amine J | 0.03% | 100 | 89.4 | 50.9 |
| 0.5% IXc | 0.27% | 0.5% amine N | 0.3% | 100 | 88.8 | 48.7 |
| 0.5% IXc | 0.25% | 0.5% amine A | 0.07% | 100 | 70.8 | 30.3 |
| 10% Zr carb. | 3.5% | 10% amine J | 1.4% | 100 | 89.4 | 55.7 |
| 10% Zr carb. | 3.4% | 10% amine N | 9% | 100 | 88.8 | 53 |
| 10% Zr carb. | 3.6% | 10% amine A | 1.2% | 100 | 73.2 | 38.6 |
| 0.5% Zr carb. | 0.23% | 0.5% amine 3 | 0.03% | 100 | 82.1 | 47.9 |
| 0.5% Zr carb. | 0.24% | 0.5% amine N | 0.3% | 100 | 81.6 | 45 |
| 0.5% Zr carb. | 0.25% | 0.5% amine A | 0.06% | 100 | 61.9 | 29.7 |
| 10% CaO | 2.9% | 10% amine J | 1.2% | 100 | 93.3 | 62.8 |
| 10% CaO | 3.1% | 10% amine N | 8.6% | 100 | 92.4 | 61.2 |
| 10% CaO | 3.3% | 10% amine A | 1.1% | 100 | 86.6 | 41.4 |
| 0.5% CaO | 0.24% | 0.5% amine 3 | 0.04% | 100 | 85.4 | 48.4 |
| 0.5% CaO | 0.25% | 0.5% amine N | 0.35% | 100 | 83.9 | 47.1 |
| 0.5% CaO | 0.25% | 0.5% amine A | 0.06% | 100 | 70.8 | 30 |

EXAMPLE 4

Stabilised phosphonite Ph-3 is prepared according to the method described in Example 1. Stability to hydrolysis is tested by storing at 50° C. and 75% of atmospheric humidity, and the content of undegraded phosphonite is tested by $^{31}$P-NMR after a storage time of 24 h and 48 h. The following Table 4 shows the amount and type of the amine and metal salt used as well as the test results.

TABLE 4

Degradation of the phosphonite Ph-3 during storage at 50° C. and 75% humidity; amount based on phosphonite

| Metal salt of Ph-3 | in product | Amine of Ph-3 | in product | Phosphite content (%) after 24 h | 48 h |
|---|---|---|---|---|---|
| 0 (unstabilised) | | 0 | 0 | 45 | 20.3 |
| 0 | 0 | 10% amine J | 6.0% | 60.8 | 40.7 |
| 0 | 0 | 10% amine N | 10% | 64.9 | 46.3 |
| 0 | 0 | 10% amine A | 6.1% | 55.4 | 32.6 |
| 10% IXc | 7.9% | 0 | 0 | 61.2 | 44.7 |
| 10% IXc | 7.4% | 10% amine J | 5.8% | 84.6 | 72.1 |
| 10% IXc | 7.5% | 10% amine N | 10% | 90.5 | 78.4 |
| 10% IXc | 7.3% | 10% amine A | 6.0% | 72.3 | 52.4 |
| 0.5% IXc | 0.4% | 0.5% amine J | 0.4% | 76.6 | 64.6 |
| 0.5% IXc | 0.4% | 0.5% amine N | 0.5% | 82.3 | 69.1 |
| 10% Zr carb. | 7.5% | 10% amine J | 5.7% | 79.4 | 67.5 |

TABLE 4-continued

Degradation of the phosphonite Ph-3 during storage at 50° C. and 75% humidity; amount based on phosphonite

| Metal salt of Ph-3 | in product | Amine of Ph-3 | in product | Phosphite content (%) after 24 h | 48 h |
|---|---|---|---|---|---|
| 10% Zr carb. | 7.5% | 10% amine N | 10% | 84.9 | 67.5 |
| 0.5% Zr carb. | 0.35% | 0.5% amine J | 0.4% | 71.3 | 60 |
| 0.5% Zr carb. | 0.35% | 0.5% amine N | 0.5% | 77.4 | 64.7 |
| 10% CaO | 7.6% | 10% amine J | 5.8% | 79.8 | 67 |
| 10% CaO | 7.5% | 10% amine N | 10% | 85.4 | 74.1 |
| 0.5% CaO | 0.3% | 0.5% amine J | 0.4% | 71.6 | 61.2 |
| 0.5% CaO | 0.3% | 0.5% amine N | 0.5% | 78 | 65 |

The test results show a markedly enhanced stability of the phosphites and phosphonites stabilised according to this invention in comparison with the unstabilised product and with products stabilised only by addition of amine or metal salts.

EXAMPLE 5

Synthesis and subsequent stabilization of Phosphite Ph-1
Ph-1 is prepared similarly as in example No. 3 of U.S. Pat. No. 5,322,871. 134 g of phosphorus trichloride are added with stirring and in the course of 3–3.5 hours to a solution of 441 g of 2,4-di-tert-butyl-6-methylphenol and 6.4 g of tetra-n-butyl-ammonium bromide in 440 g of anhydrous xylene. During this operation, the temperature is raised from initial 70°–75° C. to final 122°–125° C. The evolution of HCl is measured. The mixture is stirred at this temperature for another 0.5 hours. A slight vacuum (0.4 bar) is then applied, and the mixture is stirred at 120°–123° C. until the amount of HCl detected (>98% of theory) indicates complete reaction. Subsequently, 90 g of xylene are distilled off to remove trace impurities, the mixture is cooled to 20°–25° C. and 90 g of xylene are added again.

120 g of triethylamine are then added, followed by dropwise addition with cooling of 47 g of ethanol at constant internal temperature of 20°–25° C. The mixture is stirred at this temperature for further 3 hours.

The reaction mass is extracted twice with water (250 ml/130 ml), cellulose powder is added to the organic phase as a filter aid and drying is achieved by heating to 80°–85° C. at 100 mbar (reduced pressure). Then, 22 g of the metal salt of formula IXc

$Mg_{4.5}Al_2(OH)_{13} \cdot CO_3 \cdot 3.5H_2O$, (IXc)

(stabiliser IXc; Kyowa Chem. Ind., Osaka, Japan) are added with stirring, and a coarse filtration is carried out using a paper/fabric layer (type polyester 500 g/m²; permeability 1300 m³/(m²·h); manufacturer Dollfus and Noack, Sausheim, France). The opaque filtrate is concentrated at 80°–90° C. and final 10 mbar giving 530 g crude product as a yellow opaque oil. 22 g of anhydrous piperazine and 500 g of isopropyl alcohol are added at 50°–60° C. Crystallization is initiated at 50° C. by adding seed crystals; the temperature is kept at 50° C. for 1 h, lowered to 20°–25° C. in the course of 2 h and then kept, with stirring, at 15°–20° C. for another 2 h. Filtration, washing 4 times with a total of 350 g of isopropyl alcohol and drying at 60°–70° C. gives 440 g stabilized Ph-1 of melting point 90° C.

The thus obtained product, containing 0.002–0.004% by weight of piperazine and 1–2% by weight of metal salt of formula IXc, shows an excellent stability against hydrolysis.

What is claimed is:

1. An organic phosphite or phosphonite composition stabilized against hydrolysis comprising
   (a) 25 to 99.9% by weight, based on the total weight of the composition, of organic phosphite or phosphonite,
   (b) an effective stabilizing amount of organic amine, and
   (c) an effective stabilizing amount of acid-binding metal salt, wherein said composition comprises no organic polymers or alkali metal phosphates as further components, and wherein component (c) comprises no metal carboxylate or metal soap.

2. A composition according to claim 1, comprising 40 to 99% by weight of component (a), 0.01 to 25% by weight of component (b), and 0.05 to 15% of component (c), each based on the total weight of the composition.

3. A composition according to claim 1, wherein component (a) is an organic phosphite or phosphonite which is solid at 20° C.

4. A composition according to claim 1, wherein component (c) is an acid-binding metal salt selected from the group consisting of carbonates, bicarbonates, carboxylates, oxides, hydroxides, phosphites or borates of the metals lithium, sodium, potassium, copper, zinc, magnesium, calcium, strontium, barium, aluminium and/or zirconium, or mixtures thereof, as well as hydrotalcites and zeolites.

5. A composition according to claim 1, comprising as component (b) an amine of formula I

wherein $X^1$ and $X^2$ are each independently of the other H, $C_1$–$C_{20}$alkyl, $C_4$–$C_{20}$alkyl which is interrupted by —O— and optionally substituted by hydroxy; or $C_2$–$C_{20}$hydroxyalkyl, and $X^3$ is $C_2$–$C_{20}$alkyl, $C_4$–$C_{20}$alkyl which is interrupted by —O— and optionally substituted by hydroxy; —(CH$_2$)$_m$—NX$^1$X$^2$, or $C_2$–$C_{20}$hydroxyalkyl, or wherein $X^2$ and $X^3$ together are —(CH$_2$)$_m$—, —C$_2$H$_4$—O—C$_2$H$_4$— or —C$_2$H$_4$—NX$^1$—C$_2$H$_4$—, wherein m is an integer from 4 to 6, and $X^1$ and $X^2$ have the meanings given above;

or an aromatic amine of formula Ia

wherein D is a nitrogen atom or a group —CX$^5$—, and wherein $X^4$, $X^{4'}$, $X^{4''}$, and $X^5$ are each independently of one another hydrogen or $C_1$–$C_4$alkyl;

or a cyclic sterically hindered amine of the series of the derivatives of polyalkylpiperidines or polyalkylpiperazines, containing a group of one of the formula II or III

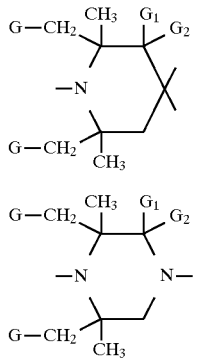

wherein G is hydrogen or methyl, and $G_1$ and $G_2$ are hydrogen, methyl or, taken together, are=O.

6. A composition according to claim 5, wherein component (b) is a sterically hindered amine of the series of the derivatives of polyalkylpiperidines, whose molecular weight or average molecular weight $\overline{M}_n$ is in the range from 300 to 10000.

7. A composition according to claim 1 consisting essentially of components (a), (b), (c) or of components (a), (b), (c) and one or two further components selected from the group consisting of phenolic and other antioxidants.

8. A process for stabilising an organic phosphite or phosphonite or a mixture of organic phosphites or phosphonites against hydrolysis, which comprises adding to said phosphite or phosphonite both an organic amine (component (b)) and an acid-binding metal salt (component (c)), wherein said process is candied out in the absence of an organic polymer or an alkali metal phosphate, and wherein component (c) comprises no metal carboxylate or metal soap.

9. A process for stabilising an organic phosphite or phosphonite or a mixture of organic phosphites or phosphonites against hydrolysis according to claim 8, such that the stabilised phosphite or phosphonite comprises 0.001 to 50% by weight of component (b) and 0.01 to 25% by weight of component (c), in each case based on the total weight.

10. A process according to claim 8, wherein components (b) and (c) are added to the solution or melt of the phosphite or phosphonite prior to the crystallisation thereof.

11. A process according to claim 10, wherein component (c) is added, followed by filtration and subsequent addition of component (b).

12. A process according to claim 10, which comprises adding a homogeneous melt, heated to 50° to 100° C., of phosphite or phosphonite, of a solvent or solvent mixture, and of 0.1 to 100% by weight (based on phosphite or phosphonite) of an amine, in which melt 0.05 to 25% by weight of acid-binding metal salt (based on phosphite or phosphonite) is dispersed, to a liquid crystallisation medium, the temperature of which during the addition is kept from 10° to 70° C. below the temperature of the melt.

13. An organic phosphite or phosphonite composition which is stabilised against hydrolysis, obtained in accordance with a process according to claim 8.

14. An organic phosphite or phosphonite composition which is stabilised against hydrolysis, obtainable in accordance with a process according to claim 10.

* * * * *